US011237164B2

(12) United States Patent
Kazakova et al.

(10) Patent No.: US 11,237,164 B2
(45) Date of Patent: *Feb. 1, 2022

(54) METHOD FOR MEASUREMENT OF TOTAL PROTEIN CONTENT AND DETECTION OF PROTEIN VIA IMMUNOASSAY IN A MICROFLUIDIC DEVICE

(71) Applicant: ProteinSimple, San Jose, CA (US)

(72) Inventors: Irina Georgievna Kazakova, San Jose, CA (US); Crystal Tran, Milpitas, CA (US); Jessica Dermody, San Jose, CA (US); Annegret Boge, Menlo Park, CA (US); Tom Weisan Yang, Cupertino, CA (US)

(73) Assignee: ProteinSimple, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/932,445

(22) Filed: Jul. 17, 2020

(65) Prior Publication Data

US 2021/0325401 A1 Oct. 21, 2021

Related U.S. Application Data

(60) Provisional application No. 63/010,436, filed on Apr. 15, 2020.

(51) Int. Cl.
*G01N 33/559* (2006.01)
*G01N 33/68* (2006.01)
(Continued)

(52) U.S. Cl.
CPC .............. *G01N 33/559* (2013.01); *C07K 1/26* (2013.01); *G01N 33/53* (2013.01);
(Continued)

(58) Field of Classification Search
CPC .............. G01N 33/6839; G01N 33/53; G01N 2550/00; G01N 33/559; G01N 27/447; C07K 1/26
(Continued)

(56) References Cited

U.S. PATENT DOCUMENTS 7,846,676 B2 12/2010 Yang et al.
7,935,489 B2 5/2011 O'Neill et al.
(Continued)

FOREIGN PATENT DOCUMENTS

WO WO 2014/138475 9/2014

OTHER PUBLICATIONS

Yeung (2009) Anal Biochem 389:89-91 (Year: 2009).*
(Continued)

*Primary Examiner* — Christopher L Chin
(74) *Attorney, Agent, or Firm* — Cooley LLP

(57) ABSTRACT

Some embodiments described herein relate to systems and methods operable to combine immunoassay and Total Protein techniques in a single sample run. Some embodiments described herein allow for multiple sequential immunoassays to be performed in the same microfluidic device. Some embodiments described herein relate to stripping reagents operable to remove primary antibodies associated with immunoassays. Such stripping reagents can allow for additional immunoassays and/or Total Protein assays to be performed on the same sample.

6 Claims, 18 Drawing Sheets

(51) Int. Cl.
*G01N 33/53* (2006.01)
*C07K 1/26* (2006.01)
*G01N 27/447* (2006.01)

(52) U.S. Cl.
CPC ....... *G01N 33/6839* (2013.01); *G01N 27/447* (2013.01); *G01N 2550/00* (2013.01)

(58) Field of Classification Search
USPC .................................. 436/501, 515; 530/412
See application file for complete search history.

(56) References Cited

U.S. PATENT DOCUMENTS

| | | | |
|---|---|---|---|
| 9,766,206 | B2 | 9/2017 | Yang et al. |
| 2003/0032035 | A1* | 2/2003 | Chatelain ......... G01N 33/54366 435/6.14 |
| 2006/0029978 | A1 | 2/2006 | O'Neill et al. |
| 2006/0249558 | A1* | 11/2006 | Roach ................ G01N 35/1065 228/101 |
| 2008/0017512 | A1 | 1/2008 | Bordunov et al. |
| 2014/0295424 | A1 | 10/2014 | Lin et al. |
| 2015/0005188 | A1* | 1/2015 | Levner ................ C12Q 1/6804 506/9 |
| 2015/0253251 | A1 | 9/2015 | McKee et al. |

OTHER PUBLICATIONS

Han, J. C. et al., "A procedure for quantitative determination of tris(2-carboxyethyl)phosphine, an odorless reducing agent more stable and effective than dithiothreitol," Anal. Biochem., Jul. 1994, 220(1):5-10.
Han, S. et al., "Inactivation of Horseradish Peroxidase by Acid for Sequential Chemiluminescent Western Blot," Biotechnol. J., Mar. 2020,15(3):e1900397.
Henry, S. et al., "Rapid one-step biotinylation of biological and non-biological surfaces," Scientific Reports (2018) 8(2845): 1-6.
Office Action for U.S. Appl. No. 16/932,441, dated Dec. 24, 2020, 11 pages.
Office Action for U.S. Appl. No. 16/932,441, dated Feb. 26, 2021, 8 pages.
Invitation to Pay Additional Fees, Partial Search Report and Provisional Opinion for International Application No. PCT/US2021/027318, dated Jul. 6, 2021, 12 pages.
Sinkala, E. et al., "Profiling protein expression in circulating tumour cells using microfluidic western blotting," Nature Communications, vol. 8, No. 1, Mar. 2017, DOI: 10.1038/ncomms14622, 12 pages.
Hughes, A. J et al., "Single-cell western blotting," Nature Methods, vol. 11, No. 7, Jul. 2014, pp. 749-755.
Kang, C-C et al., "Single cell-resolution western blotting," Nature Protocols, vol. 11, No. 8, Jul. 2016, pp. 1508-1530.
Labib, M. et al., "Single-cell analysis targeting the proteome," Nature Reviews Chemistry, vol. 4, No. 3, Feb. 2020, pp. 143-158.
Rosas-Canyelles, E. et al., "Single-embryo and single-blastomere immunoblotting reports protein expression heterogeneity in early-stage preimplantation embryos," bioRxiv, Jun. 2018, 19 pages.
Rosas-Canyelles, E. et al., "Multimodal detection of protein isoforms and nucleic acids from mouse pre-implantation embryos," Nature Protocols, vol. 16, No. 2, Jan. 2021, pp. 1062-1088.
International Search Report and Written Opinion for International Application No. PCT/US2021/027318, dated Sep. 1, 2021, 17 pages.

* cited by examiner

METHOD FOR MEASUREMENT OF TOTAL PROTEIN CONTENT AND DETECTION OF PROTEIN VIA IMMUNOASSAY IN A MICROFLUIDIC DEVICE

CROSS-REFERENCE TO RELATED APPLICATIONS

This application claims priority to and the benefits of U.S. Provisional Patent Application No. 63/010,436, filed Apr. 15, 2020, the entire disclosure of which is hereby incorporated by reference in its entirety.

FIELD

Embodiments described herein generally related to capillary electrophoresis methods for performing immunoassays and/or protein quantity assays on samples. Stripping reagents are disclosed that are operable to remove antibodies associated with immunoassays such that additional assays can be performed on the same sample.

BACKGROUND

An important part of protein research includes characterizing proteins within a heterogeneous sample, such as a cell lysate that can include of thousands of proteins. A Western blot is a commonly used immunoassay-based method used to analyze specific proteins within these complex samples, using the specificity of antibodies to identify protein(s) of interest. When performing immunoassays in a western blot format, it has increasingly become more important to quantify the resulting immunoassay signal. One method for quantification is to normalize the immunoassay signal to the total protein content in the sample. This has increasingly been requested by journals when publishing western blot results to ensure data accuracy and precision.

Existing systems are operable to provide fully automated microfluidic-based (e.g., capillary-based) immunoassays, such as ProteinSimple's® Simple Western® instrument. Some such systems are capable of combining an immunoassay(s) with size separation similar to traditional gel-based western blots in a capillary. The sample, separation matrix, stacking matrix, antibodies and reagents can be loaded automatically. The instrument can be operable to aspirate a separation matrix and then a stacking matrix into each capillary. Next, a sample, which can contain a heterogeneous protein mixture can be loaded, and capillaries can be brought into contact with running buffer. Voltage can be applied to enable separation by molecular weight or other suitable characteristic. Once the separation is complete, UV light can immobilize the proteins to the capillary wall. Immunoprobing of the proteins can be carried out, for example, with proteins immobilized and the matrix cleared from the capillary. Additionally, some existing systems are operable to provide a "Total Protein" assay, which can be carried out through biotinylation of proteins immobilized to a capillary's inner surface, followed by detection of horseradish peroxidase (HRP) conjugated streptavidin and a chemiluminescent reaction.

A need, however, exists for a method that permits chemiluminescence detection for both the immunoassay and Total Protein readout in the same capillary. In addition, it is desirable to increase multiplexing capabilities beyond the number of detection modalities/channels.

SUMMARY

Some embodiments described herein relate to systems and methods operable to combine immunoassay and Total Protein techniques in a single sample run. Instruments having both chemiluminescence and fluorescence detection capabilities, such as Jess® by ProteinSimple® can provide a "Protein Normalization" method whereby a fluorescent dye is covalently attached to all separated and immobilized protein molecules via, for example, NHS-ester amine coupling. In this way, a specific target can be measured, for example, using chemiluminescence associated with an immunoassay, while a measure of the total protein loaded is determined from the fluorescence signal. Known techniques for protein normalization typically have similar dynamic range as typical western blot-style immunoassays and cannot be multiplexed in the same capillary in which an immunoassay has been run using chemiluminescence detection. In contrast, embodiments of Protein Normalization described herein can be multiplexed in the same capillary with a chemiluminescence immunoassay, and may have a decreased or different dynamic range compared to the immunoassay signal.

In addition to performing a Total Protein and immunoassay in the same capillary, some embodiments described herein allow for multiple sequential immunoassays to be performed in the same capillary. Instruments that have both chemiluminescence and fluorescence detection capabilities (e.g., ProteinSimple's® Jess®) allow for "multiplexed" detection, i.e., detection of multiple targets within a capillary using a single mixture of antibodies conjugated with moieties for either chemiluminescence or fluorescence detection. However, combining antibodies in a single mixture constrains which antibodies can be mixed, for example, due to non-specific signal resulting from cross-reactivity of the antibodies used for the immunoassays or incompatible dynamic range for the antibodies when used in the same capillary (e.g., different dynamic range for chemiluminescence versus fluorescence).

Embodiments described herein relate to the use of a Total Protein assay and/or a second immunoassay in the same capillary as a western blot-style immunoassay enabling high sensitivity total protein measurements and immunoassays combined with the low sample requirement and high throughput capabilities previously demonstrated with Simple Western technology.

DETAILED DESCRIPTION

Figure 1A:
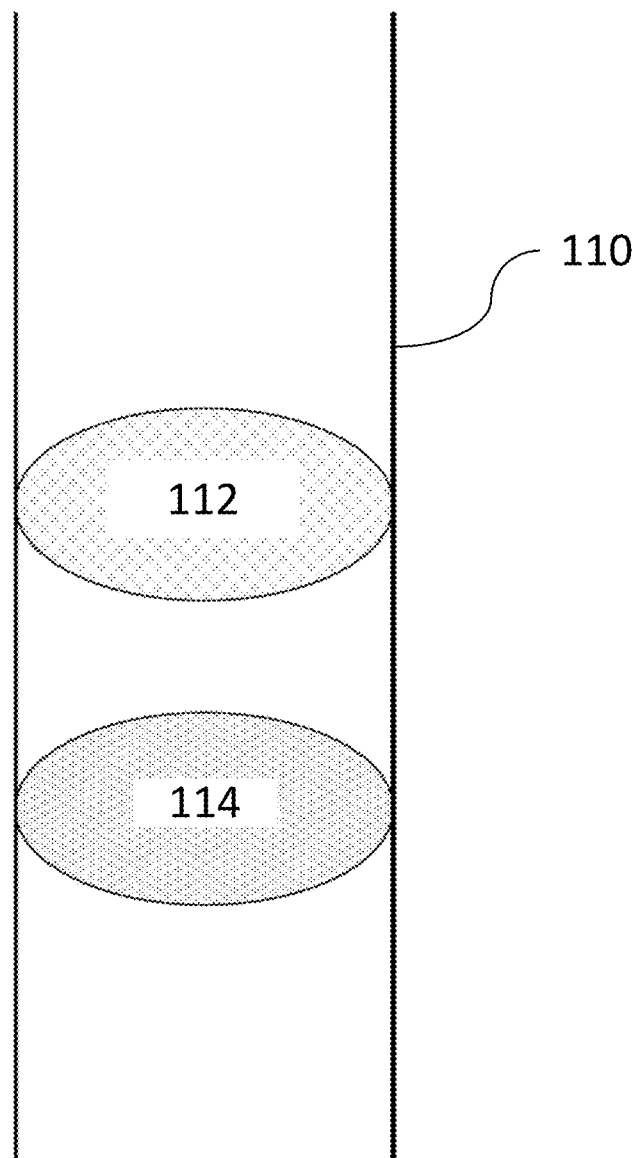
FIGS. 1A-1H illustrate events occurring in a stripping and immunoassay reprobing method, according to an embodiment.

Some embodiments described herein relate to methods suitable for performing multiple immunoassays on a sample separated via electrophoresis carried out in a capillary or other suitable microfluidic device. The sample can be separated such that at least a first analyte and a second analyte are separated into different bands. The first analyte and the second analyte can be immobilized in the capillary. A first primary antibody configured to selectively bind to the first analyte (and optionally, to not bind to the second analyte) can be introduced into the capillary. A first secondary antibody configured to selectively bind to the first primary antibody can be introduced into the capillary. The first analyte can be detected based on an optical characteristic associated with the first secondary antibody. For example, the first secondary antibody can be conjugated to horseradish peroxidase (HRP) and the first analyte can be detected based on a chemiluminescence reaction associated with the HRP. A stripping reagent configured to remove the first primary antibody from the first analyte can be introduced into the capillary. The first analyte and the second analyte can remain immobilized in the capillary after the stripping reagent is introduced and the first primary antibody (along with the first secondary antibody and/or HRP) is removed. A second primary antibody configured to bind to the second analyte can then be introduced, for example, after the introduction of the stripping reagent. A second secondary antibody configured to bind to the second primary antibody can be introduced, and the second analyte can be detected based on an optical characteristic associated with the second secondary antibody (e.g., a chemiluminescent reaction and/or a fluorescent tag).

Some embodiments described herein relate to methods suitable for performing an immunoassay and a Total Protein assay on a sample separated via electrophoresis carried out in a capillary or other suitable microfluidic device. Analytes from the sample can be separated and immobilized in the capillary. A molecule having a reactive moiety configured to non-specifically bind to proteins, such as biotin, can be introduced into the capillary. Similarly stated and for example, the proteins can be biotinylated. A primary antibody configured to bind to at least a subset of analytes can be introduced to the capillary. A secondary antibody configured to bind to the primary antibody can be introduced. The subset of analytes can be detected based on an optical characteristic associated with the secondary antibody. A stripping reagent configured to remove the primary antibody from the subset of analytes can be introduced. The immobilized analytes can remain in the capillary after the stripping reagent is introduced and the primary antibody (along with the secondary antibody) is removed. An optically detectable agent configured to bind to the molecule can be introduced into the capillary. In the example in which the molecule is biotin, streptavidin can be introduced. The streptavidin can be conjugated to HRP or otherwise made optically detectable. All biotinylated analytes (e.g., all proteins) in the capillary can be detected based on an optical signal associated with the optically detectable agent. The optical characteristic associated with the secondary antibody (e.g., an immunoassay signal) can be normalized based on the optical signal associated with the optically detectable agent (e.g., a Total Protein signal). In some embodiments, it can be important that the events of this paragraph be performed in the order in which they are described.

Normalizing an immunoassay signal (or other suitable signal) can improve the ability of the instrument and/or analyst to accurately compare measured quantities from different samples by eliminating the influence of certain uncontrolled differences between the samples that are not the subject of study. For immunoassays, normalizing to total protein content in each sample can eliminate the influence of variability due to the sample composition (e.g. cell count, lysate dilution) or pipetting errors. Additionally, normalizing to total protein content is advantageous to normalizing to a specific housekeeping protein (e.g. beta actin or beta tubulin) as these proteins' expression levels can be affected by an experimental treatment or their immunoassay signal may not be in the same linear dynamic range as that of the target protein. In one embodiment, a normalization is performed by dividing the amount of a specific protein determined by an immunoassay in a capillary by the ratio of the total protein in the capillary to the total protein in a reference capillary.

Some embodiments described herein relate to a formulation of a stripping reagent. The stripping reagent can include a buffer, Tris(2-carboxyethyl)phosphine hydrochloride (TCEP), and a detergent. The stripping reagent can have a pH below 5.

Some embodiments described herein relate to a method for using a stripping reagent that includes TECP and has a pH between 3.0 and 4.5. The stripping reagent can be used to remove a first primary antibody associated with an immunoassay from an analyte. The analyte can be electrophoretically separated and immobilized in a capillary. The first primary antibody and a first secondary antibody associated with the immunoassay can be introduced into the capillary. After the first primary antibody is removed from the capillary using the stripping reagent, streptavidin or another suitable reagent configured to bind to biotinylated proteins and/or a second primary antibody configured to bind to an analyte in the sample can be introduced into the capillary.

Stripping and Reprobing Methods

Stripping and reprobing can allow users to analyze the same immobilized proteins, in the same capillary and same run, thereby saving time, money and precious samples.

FIGS. 1A-1H illustrate events occurring in a stripping and reprobing method, according to an embodiment. Stripping and reprobing can be used to perform two or more immunoassays on a single sample in sequence (e.g., reusing the separated and immobilized sample and/or without requiring additional sample to be (re)loaded and/or (re)separated for each immunoassay). FIG. 1A, is a schematic illustration of a sample that has been separated and immobilized to a surface of a capillary 110. For example, the analyte can be covalently bound to the surface of a capillary 110, for example, using the devices and/or method shown and described in U.S. Pat. No. 7,846,676 and/or U.S. Patent Application Pub. No. 2008/0017512, the entire disclosure of each of which is hereby incorporated by reference in its entirety. As shown, the sample has been separated into two bands 112 and 114. Each band represents a distinct analyte species and is present in a distinct portion of the capillary 110. It should be understood that the sample can contain any number of analyte species and/or be separated into any number of bands.

As used herein, the term "analyte" refers to any molecule or compound to be separated via electrophoretic techniques and/or detected with the methods, apparatus and systems provided herein. Suitable analytes include, but are not limited to, small chemical molecules such as, for example, environmental molecules, clinical molecules, chemicals, pollutants, and/or biomolecules. More specifically, such chemical molecules can include, but are not limited to pesticides, insecticides, toxins, therapeutic and/or abused drugs, antibiotics, organic materials, hormones, antibodies, antibody fragments, antibody-molecule conjugates (e.g., antibody-drug conjugates), antigens, cellular membrane antigen, proteins (e.g., enzymes, immunoglobulins, and/or glycoproteins), nucleic acids (e.g., DNA and/or RNA), lipids, lectins, carbohydrates, whole cells (e.g., prokaryotic cells such as pathogenic bacteria and/or eukaryotic cells such as mammalian tumor cells), viruses, spores, polysaccharides, glycoproteins, metabolites, cofactors, nucleotides, polynucleotides (comprising ribonucleic acid and/or deoxyribonucleic acid), transition state analogs, inhibitors, receptors, receptor ligands (e.g., neural receptors or their ligands, hormonal receptors or their ligands, nutrient receptors or their ligands, and/or cell surface receptors or their ligands), receptor-ligand complexes, nutrients, electrolytes, growth factors and other biomolecules and/or non-biomolecules, as well as fragments and combinations thereof. In some embodiments, the analyte is a protein or a protein complex, and the sample is a cellular lysate or a purified protein. Other suitable analytes can include aggregates, agglomerates, floc, and/or dispersed phase droplets or particles of colloids and/or emulsions. Once separated, a "band" of analytes is referred to herein as an "analyte species."

As used herein, the term "sample" refers to a composition that contains an analyte or analytes to be detected. A sample, in some embodiments, is heterogeneous, containing a variety of components (e.g., different proteins) or homogenous, containing one component (e.g., a population of one protein). In some instances, a sample can be naturally occurring, a biological material, and/or a manufactured material. Furthermore, a sample can be in a native (e.g., a cell suspension) or denatured form (e.g., a lysate). In some instances, a sample can be a single cell (or contents of a single cell, e.g., as a cellular lysate from the single cell, or a purified protein) or multiple cells (or contents of multiple cells, e.g., as a cellular lysate from the multiple cells, or a purified protein from the multiple cells), a blood sample, a tissue sample, a skin sample, a urine sample, a water sample, and/or a soil sample. In some instances, a sample can be from a living organism, such as a eukaryote, prokaryote, mammal, human, yeast, and/or bacterium or the sample can be from a virus.

Samples can be separated by any suitable mobility parameter such as charge, molecular weight, electrophoretic mobility (e.g., influenced by molecular weight, characteristic length, area, or volume, oligonucleotide length, or other suitable characteristic), isoelectric point and/or the like. For example, in some embodiments, a sample is subjected to an electrophoretic separation in a capillary tube comprising a separation matrix, based on a mobility parameter such as molecular weight or the like. The capillary tube can include a separation matrix, which can be added in an automated fashion. The separation matrix, in some embodiments, is an isoelectric separation matrix, and has similar or substantially the same properties of a polymeric gel, used in conventional electrophoresis experiments, such as a pH gradient. Capillary electrophoresis in the separation matrix is analogous to separation in a polymeric gel, such as a polyacrylamide gel or an agarose gel, where molecules are separated on the basis of the mobility parameter of the molecules in the sample, by providing a porous passageway through which the molecules can travel.

Figure 1B:
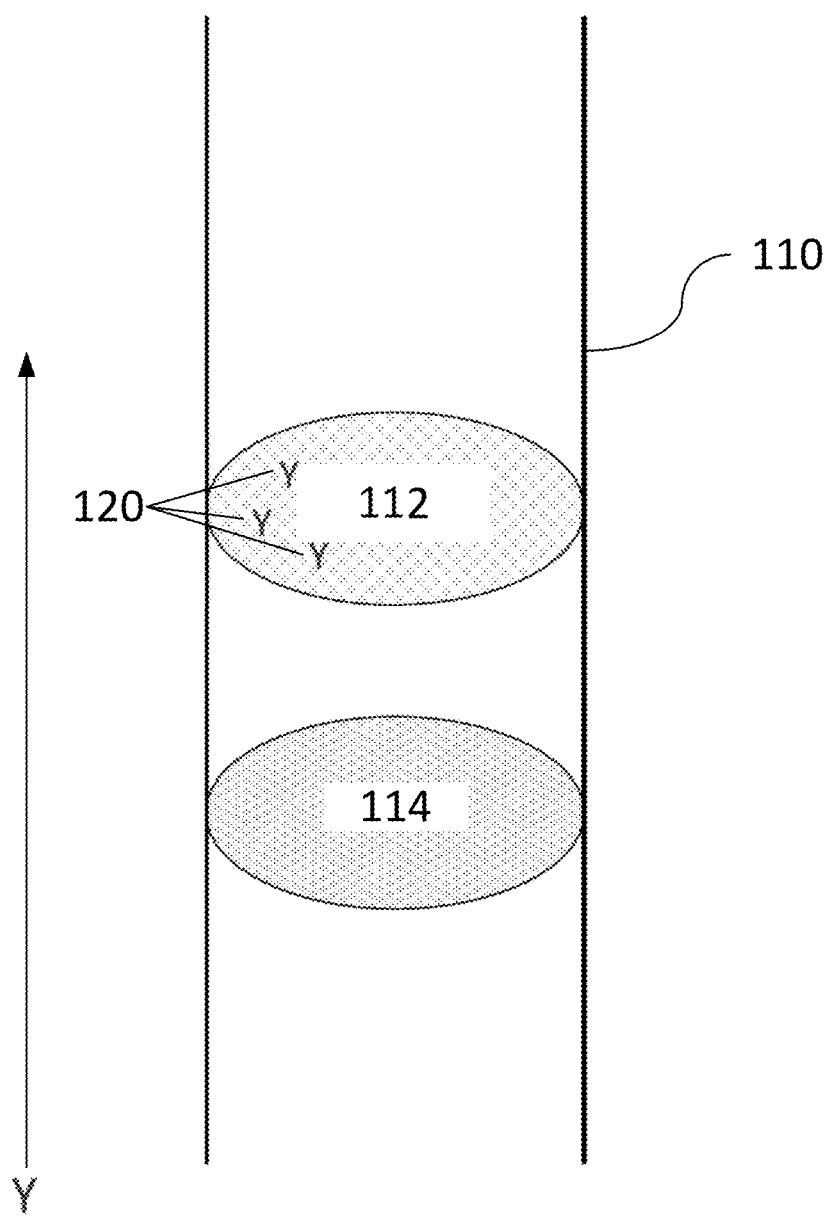

As shown in FIG. 1B, first primary antibody 120 can be introduced into a capillary 110, for example, after separation and immobilization of the analytes. In some instances, after an analysis is initiated, an instrument can be operable to automatically separate, immobilize, and/or introduce the first primary antibody 120 without any further user intervention. The first primary antibody 120 can be configured to selectively bind to one or more analyte species within the capillary 120. That is, in some instances, the first primary antibody 120 can be configured to bind to certain target analytes within the sample/capillary 120 while not binding to other (e.g., non-target) analytes. In some instances, unbound first primary antibody can be removed, for example, after an incubation period, in a washing step.

Figure 1C:
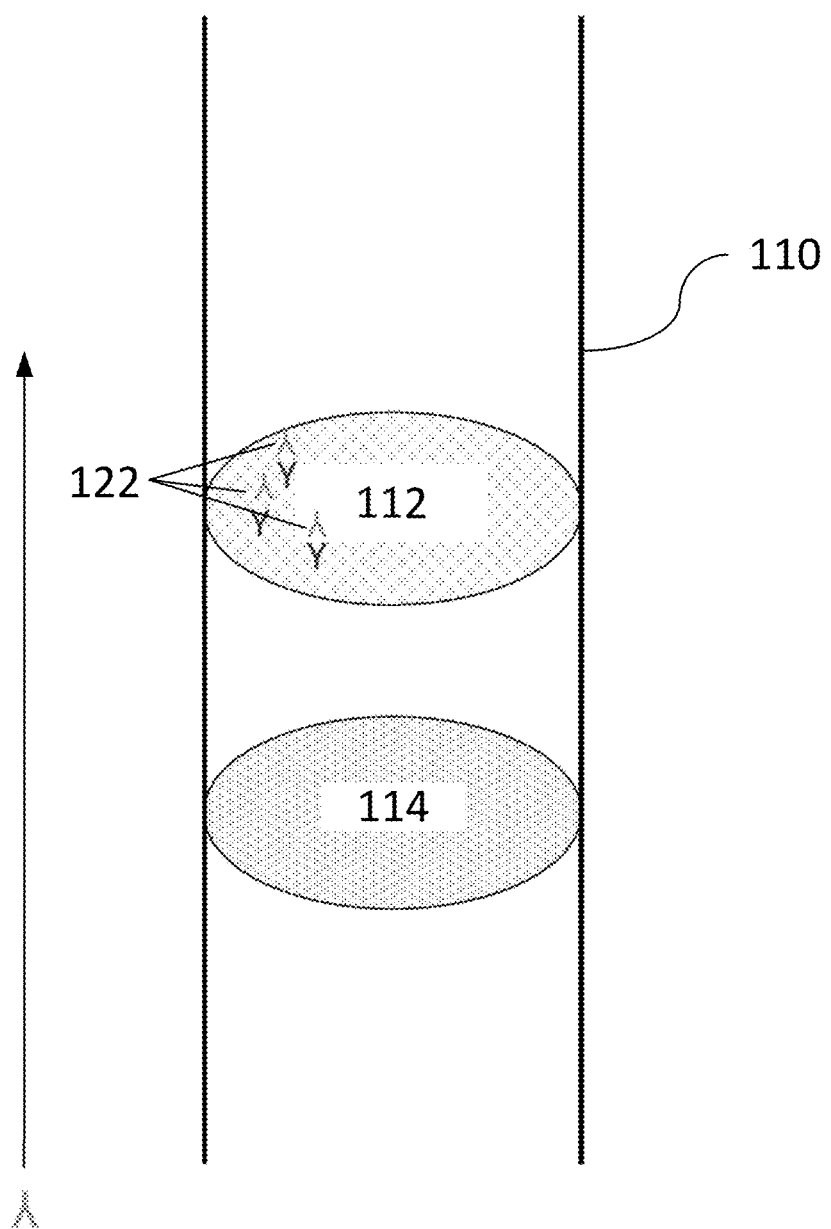
Figure 1D:
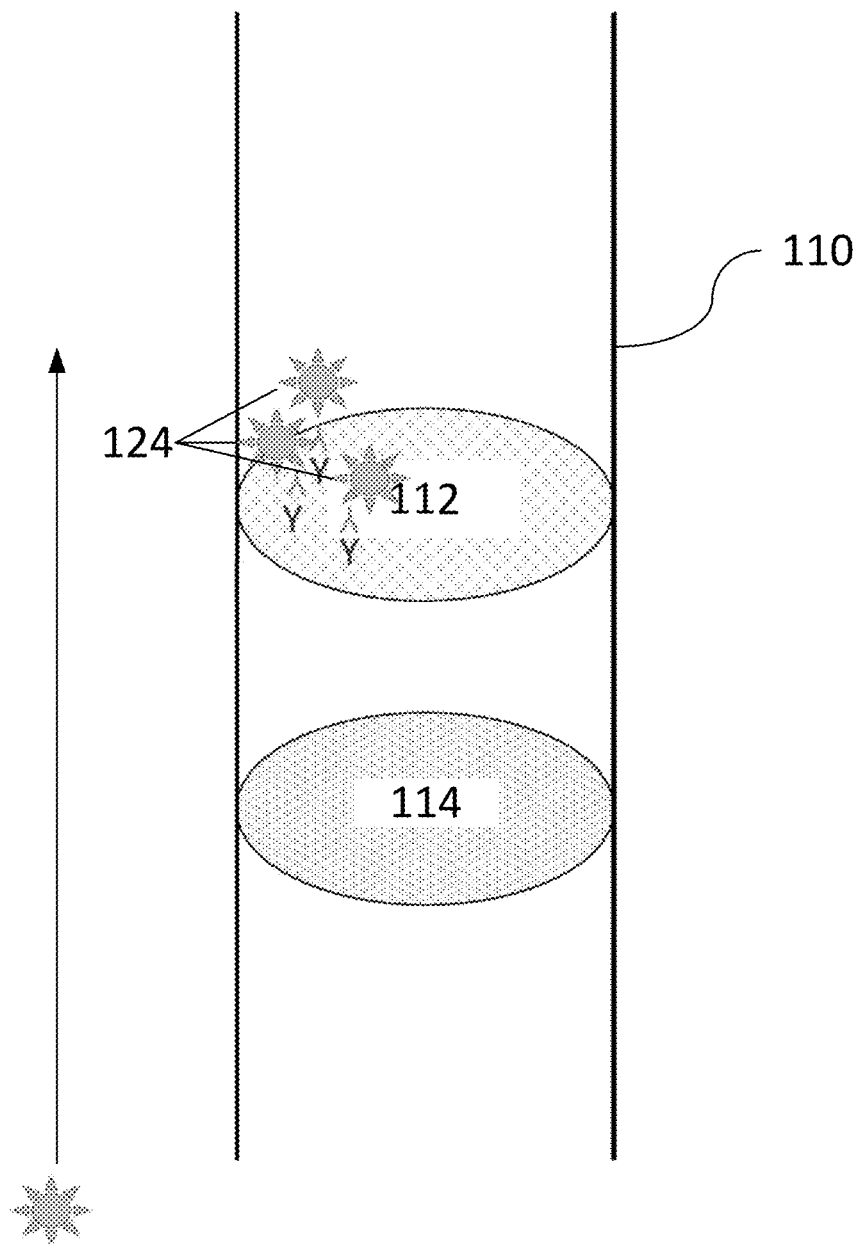

A first secondary antibody 122 can be introduced into the capillary 110, as shown in FIG. 1C. The first secondary antibody 122 can be configured to bind to the first primary antibody 120. In some instances, unbound first secondary antibody 122 can be removed, for example, after an incubation period, in a washing step. As shown in FIGS. 1C and 1D, the secondary antibody 122 is conjugated with HRP prior to being introduced into the capillary 110. As shown in FIG. 1D, a chemiluminescent substrate 124, such as 3,3',5, 5'-Tetramethylbenzidine (TAB), 3,3'-Diaminobenzidine (DAB), luminol, peroxide, or any other suitable chromogenic and/or (enhanced) chemiluminescent substrate is introduced into the capillary. The HRP conjugated to the secondary antibody 122 can catalyze the chemiluminescent substrate 124, producing an optical signal.

Figure 1E:
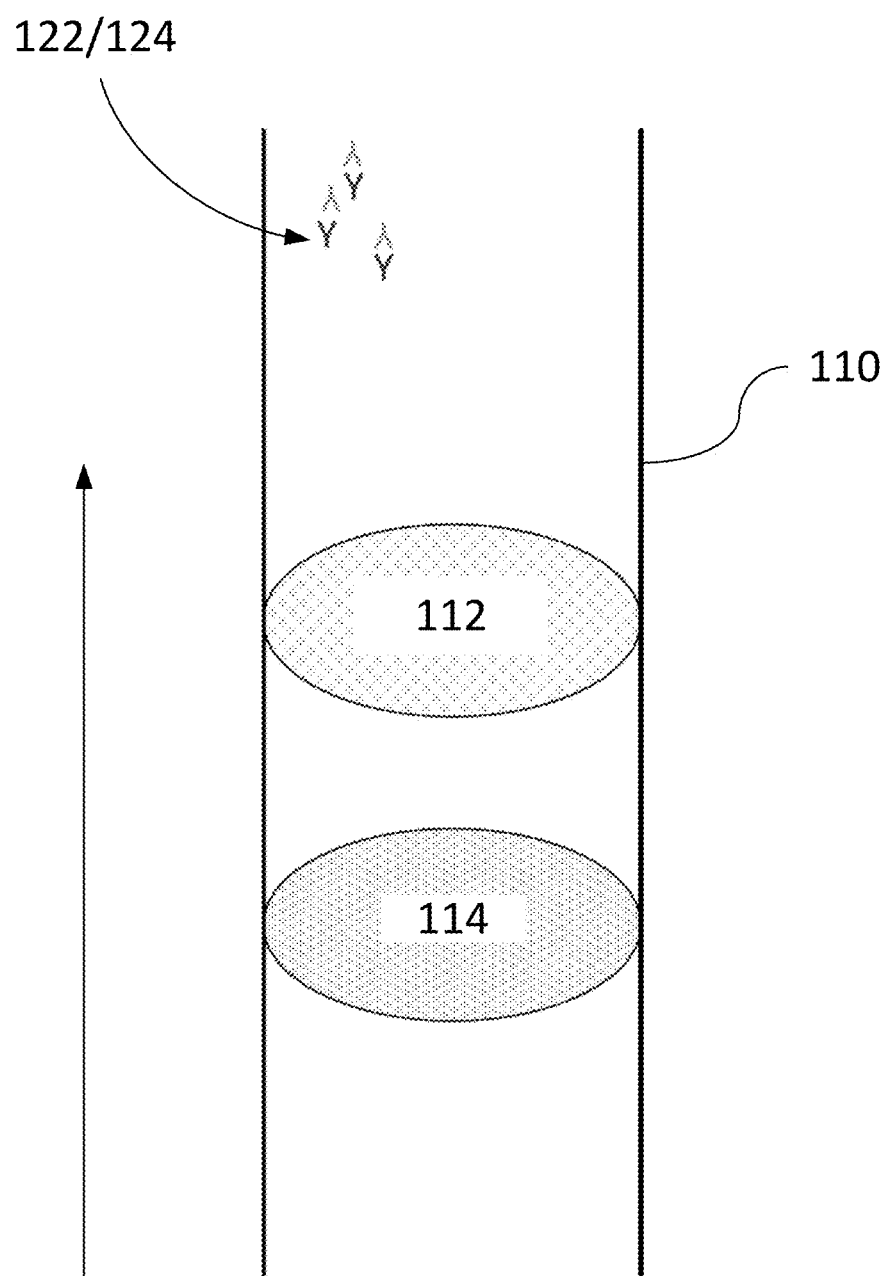

The first analyte 112/analyte species labeled with the first primary antibody 120 can be detected based on an optical characteristic associated with the first secondary antibody 122. For example, a chemiluminescent reaction associated with HRP conjugated to the first secondary antibody 122 can be detected and/or recorded by a CCD camera or another suitable detector in an image or a series of images taken over time. After detecting analyte/analyte species labeled with the first primary antibody 120, a stripping reagent can be introduced into the capillary 110, as shown in FIG. 1E. The stripping reagent can be operable to remove the first primary antibody 120, the first secondary antibody 122, and/or optically detectable agent 124 while retaining the immobilized samples for another round of immunoassay.

Figure 1F:
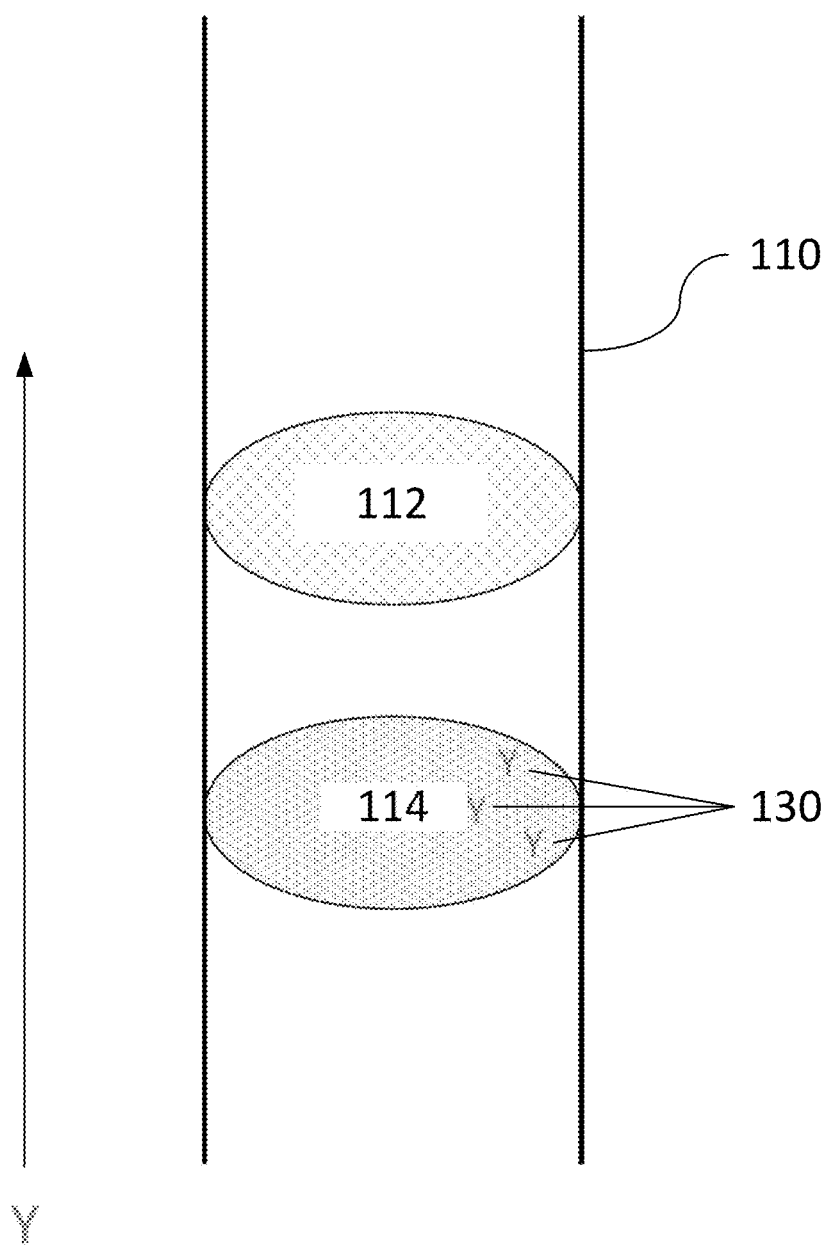
Figure 1G:
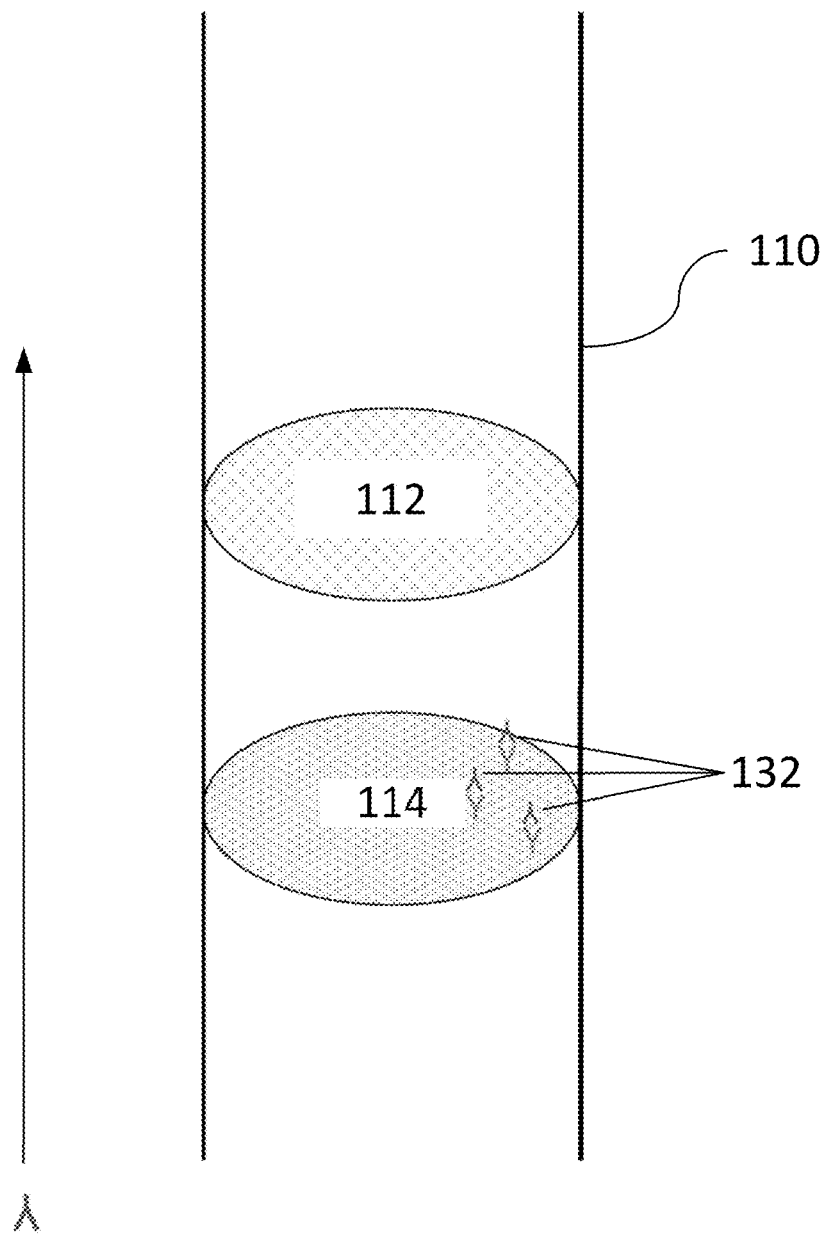
Figure 1H:
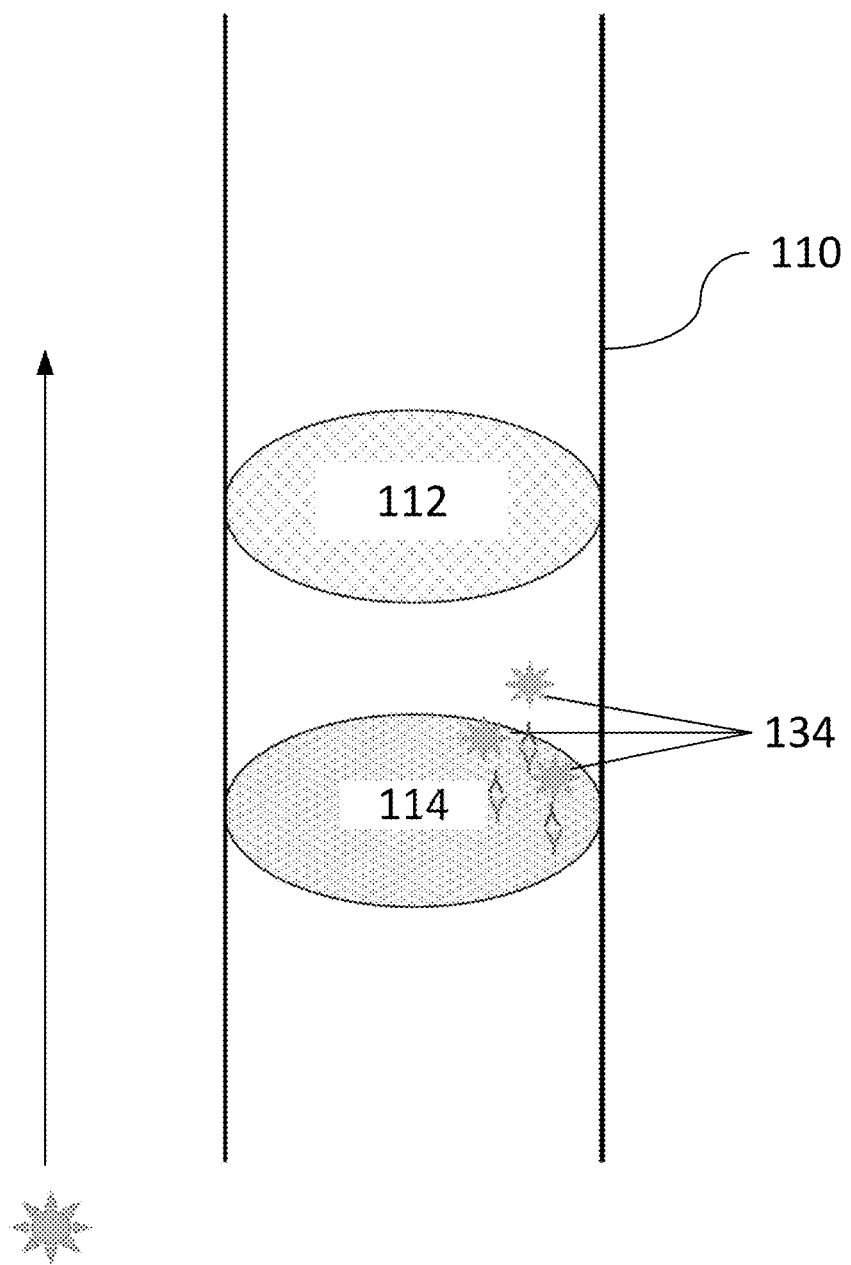

FIGS. 1F-1H then repeat the above steps with a second primary antibody 130, second secondary antibody (labeled with HRP) 132 and subsequent second detection step. The second primary antibody 130 is configured to selectively bind to the second analyte 114, and the second secondary antibody 132 is configured to bind to the second primary antibody 130. Typically the second primary antibody 130 is configured to selectively bind to a different analyte than the first primary antibody 120, but in some instances the second primary antibody 130 can be the same as the first primary antibody 120, for example, to assess the repeatability, stability, or characteristics of an assay. The second secondary antibody 132 can be the same antibody as the first secondary antibody 122 or can be a different secondary antibody. Optionally, the second primary antibody 130 and/or the second secondary antibody 132 can be introduced after the stripping agent has removed the first primary antibody 110, which can allow for sequential and distinct immunoassays to be performed on a single sample. For example, the first secondary antibody and the second secondary antibody can both be HRP-labeled and configured to produce optically indistinguishable signals in the presence of chemiluminescent substrate. By stripping the first primary antibody 120 and first secondary antibody 122 after detecting the first analyte 112 and before introducing the second secondary antibody 132, different analytes can be detected using the same optically detectable agent(s).

Although FIGS. 1A-1H depict the first primary antibody 120 and the second primary antibody 130 selectively binding to different (separated) analyte species, in other embodiments the first primary antibody 120 and the second primary antibody 130 can be configured to selectively bind to different epitopes of an electrophoretically undifferentiated analyte species.

A chemiluminescent substrate 134 can be introduced into the capillary 110 such that the HRP-labeled secondary antibody 132, and therefore the second analyte 114/analyte species can be detected based on an optical signal associated with the HRP/chemiluminescent substrate interaction.

As would be readily apparent to one skilled in the art, additional stripping and reprobing steps are possible and alternate detection modalities (color detection, fluorescence detection, etc.) can be used in addition to or instead of chemiluminescence detection. While FIGS. 1A-1H describes two sequential immunoassays that detect two distinct protein species via chemiluminescence, one skilled in the art would readily understand that an alternate embodiment could employ two different antibodies for the same target or two different epitopes of the same protein. In addition, fluorescence detection, absorbance or any common detection method may be employed, including combinations of multiple detection modes.

In addition, while FIGS. 1A-1H depict the use of primary antibodies configured to selectively bind to certain target analytes, HRP-labeled secondary antibodies configured to bind to primary antibodies, and chemiluminescent substrates, a skilled artisan will understand that other detection techniques are possible. For example, as discussed below with reference to FIG. 2D, the secondary antibody can be fluorescently labeled, rather than HRP-labeled. In such an embodiment, a separate chemiluminescent substrate may not be necessary. In such an embodiment the fluorescently labeled secondary antibody can be excited by the instrument and its emissions detected. In yet other embodiments, a primary antibody can be labeled with HRP, a fluorescent tag, or otherwise be optically detectable (e.g., via native fluorescence or absorbance techniques). In such an embodiment a separate secondary antibody may not be necessary. In yet other embodiments, tertiary, quaternary, etc. agents may be employed. For example, a secondary antibody can be biotinylated and tertiary streptavidin conjugated with an optically detectable agent (e.g. HRP or a fluorescent tag) can increase the detectable signal associated with an analyte. A skilled artisan would further understand that different detection techniques can be used to evaluate different analyte species. For example, the first analyte species 112 can be detected as shown and described with reference to FIGS. 1B-1D (e.g., through the use of a primary antibody, a HRP-conjugated secondary antibody, and a chemiluminescent substrate), while the second analyte species 114 can be detected through the introduction of a fluorescently labeled primary antibody without the use of HRP or secondary antibodies.

In some embodiments some or all of the events shown and described with reference to FIGS. 1A-1H can be performed automatically and/or without additional user intervention, other than an indication to initiate the immunoassay(s). Additionally, the events described with reference to FIGS. 1A-1H can be performed in the order described.

FIGS. 2A-2H illustrate events occurring in a stripping and reprobing method, according to an embodiment. The embodiment illustrated in FIGS. 2A-2H can be used to combine one or more immunoassays with a Total Protein assay. As shown, the Total Protein assay can be performed in the same capillary and/or on the same sample as a western-blot style immunoassay. In some instances it may be preferable to perform the events illustrated in FIGS. 2A-2H and described below in the order shown, which reduces reagent deterioration.

Figure 2A:
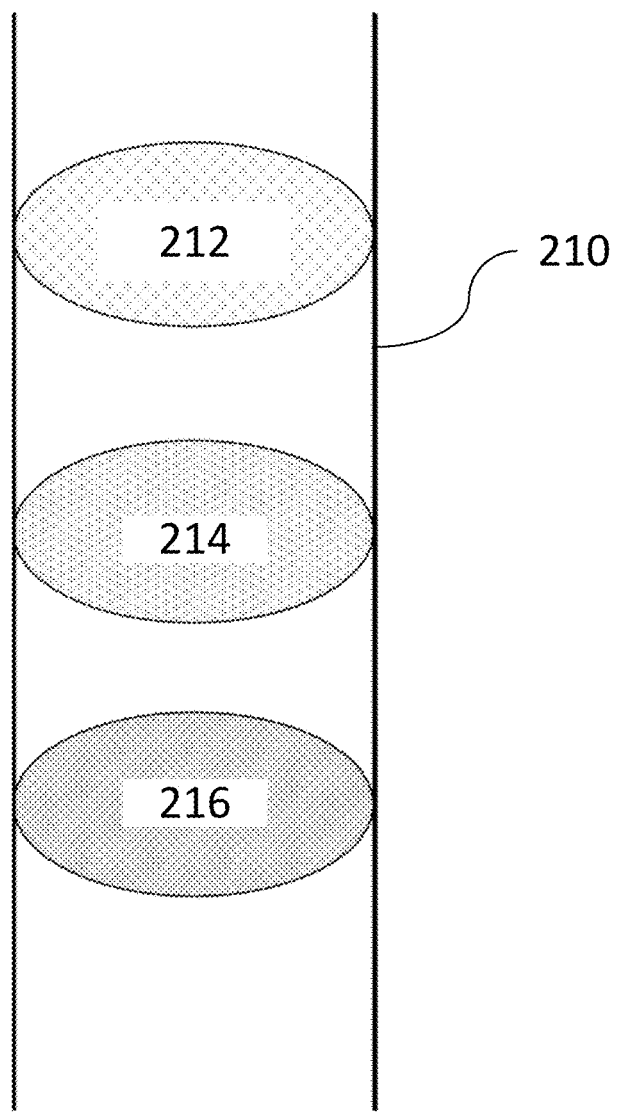
FIGS. 2A-2H illustrate events occurring in a stripping and Total Protein reprobing method, according to an embodiment.

FIG. 2A, is a schematic illustration of a sample that has been separated and immobilized to a surface of a capillary 210. For example, the analyte can be covalently bound to the surface of a capillary 210. As shown, the sample has been separated into three bands 212, 214, and 216. Each band represents a distinct analyte species. It should be understood that the sample can contain any number of analyte species and/or be separated into any number of bands. For example, in some instances, the sample can be a homogenous mixture of a single analyte species.

Figure 2B:
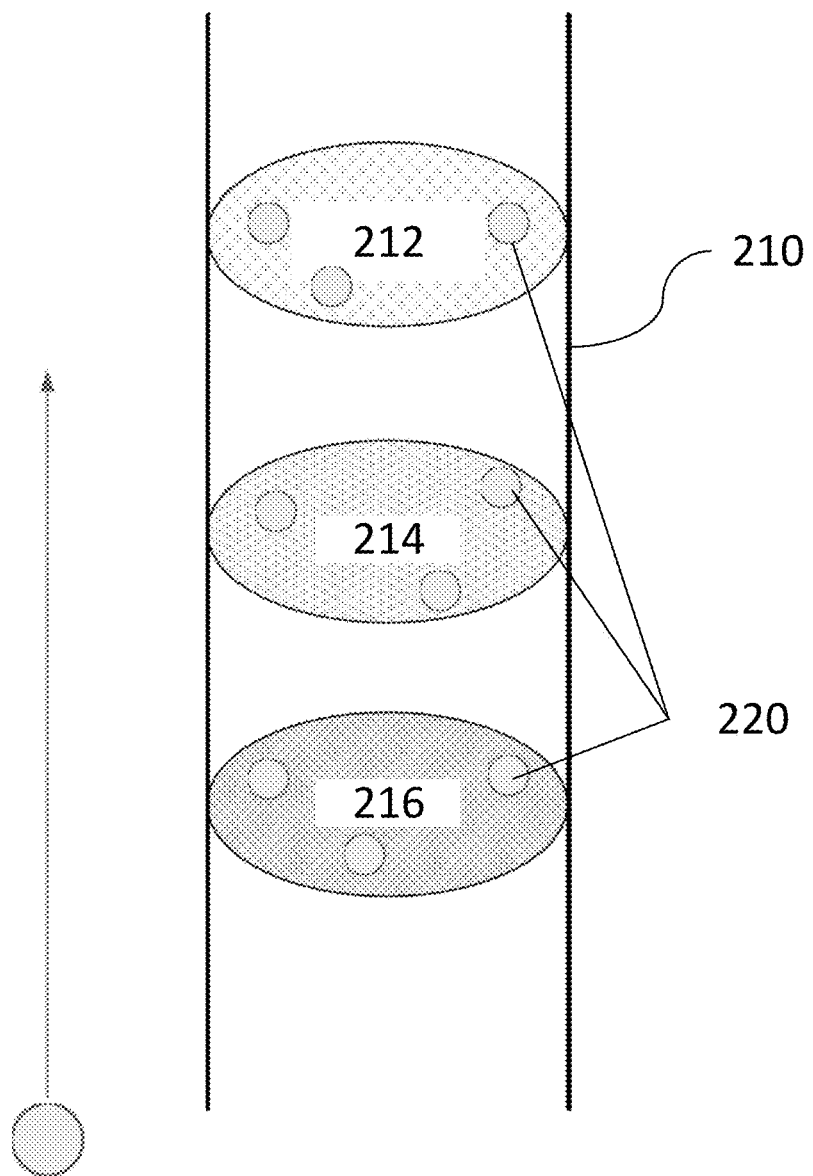

After the sample has been separated and/or immobilized, a biotinylation reagent 220 can be introduced into the capillary 210, as shown in FIG. 2B. The biotinylation reagent 220 can be configured to bind to all proteins such that a Total Protein assay can be performed (as discussed in further detail below)—that is, such that a total quantity of protein in the sample/capillary 210 can be determined. It can be preferable to add the biotinylation reagent 220 to the capillary 210 prior to performing any immunoassay, as biotinylation reagents may not be stable enough to be introduced in the capillary post-immunoassay. For example, in some instances, a user can load the biotinylation reagent (e.g., onto a sample plate) immediately prior to initiating the run (e.g., less than 20 minutes before the sample is introduced into the capillary) as in some situation, the biotinylation reagent may begin to degrade once loaded. In some instances, the biotinylation reagent is introduced into the capillary immediately after the sample has been separated and/or immobilized (e.g., within 5 minutes of immobilizing and/or within 90 minutes of introducing the sample into the capillary). Optionally, excess (e.g., unbound) biotin can be washed from the capillary after it is introduced. As discussed in further detail herein, the instrument can be operable to run a reference sample in a parallel lane. Similarly stated, the instrument can be operable to load the same or different samples into multiple capillaries, including capillary 210 and at least one reference capillary (not shown). The biotinylation reagent 220 can be introduced into the reference capillary simultaneous to the introduction of biotinylation reagent into capillary 210 or, for example, within 5 minutes of introduction of biotinylation reagent into capillary 210. Typically, given the stability profile of the biotinylation reagent, it is introduced into the reference capillary and capillary 210 before any immunoassay(s) is performed on sample in capillary 210.

Figure 2C:
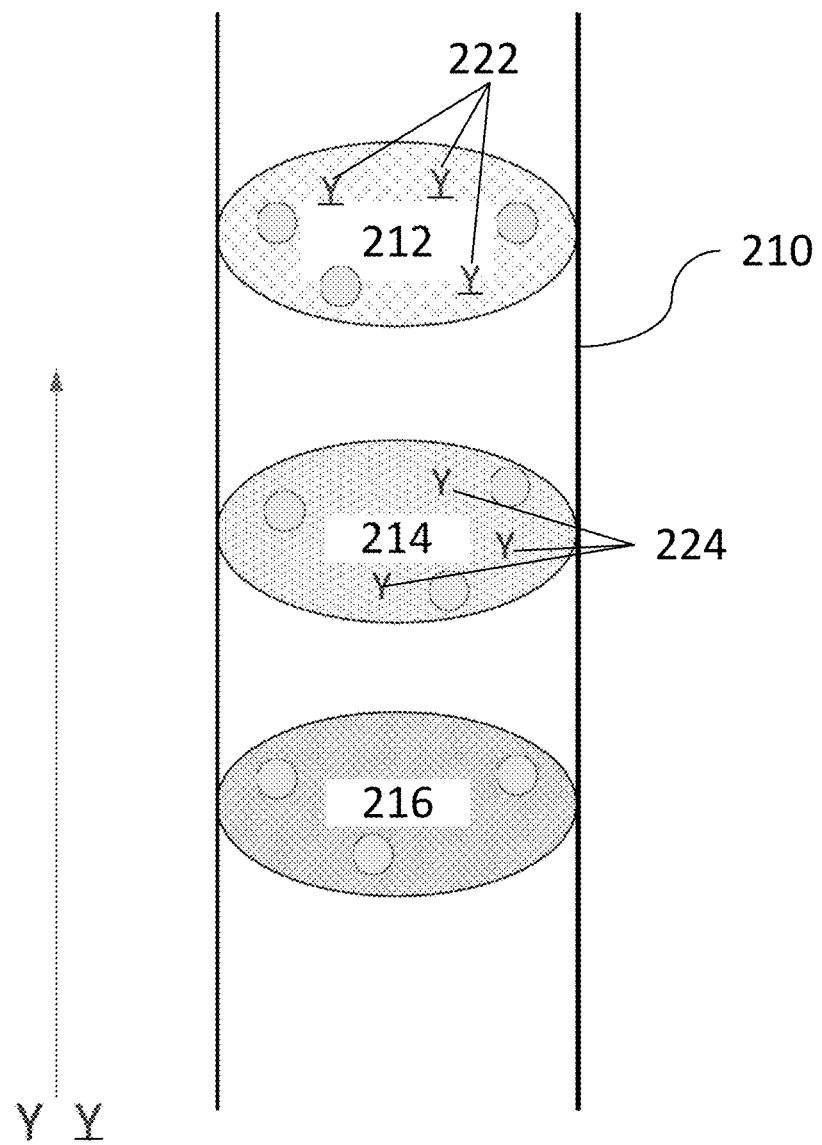

An immunoassay can be performed on the sample immobilized in the capillary 210 by introducing one or more primary antibodies. As shown in FIG. 2C, a first primary antibody 222 configured to selectively bind to a first analyte species 212 and a second primary antibody 224 configured to selectively bind to a second analyte species 214 are introduced. It should be understood, however, that any number of primary antibodies with any suitable selective binding characteristics can be introduced. Additionally, the first primary antibody 222, the second primary antibody 224, and/or any other primary antibodies can be introduced sequentially or substantially simultaneously (e.g., mixed together and/or drawn from a common reagent reservoir). Optionally excess (e.g., unbound) primary antibody can be washed from the capillary 210.

Figure 2D:
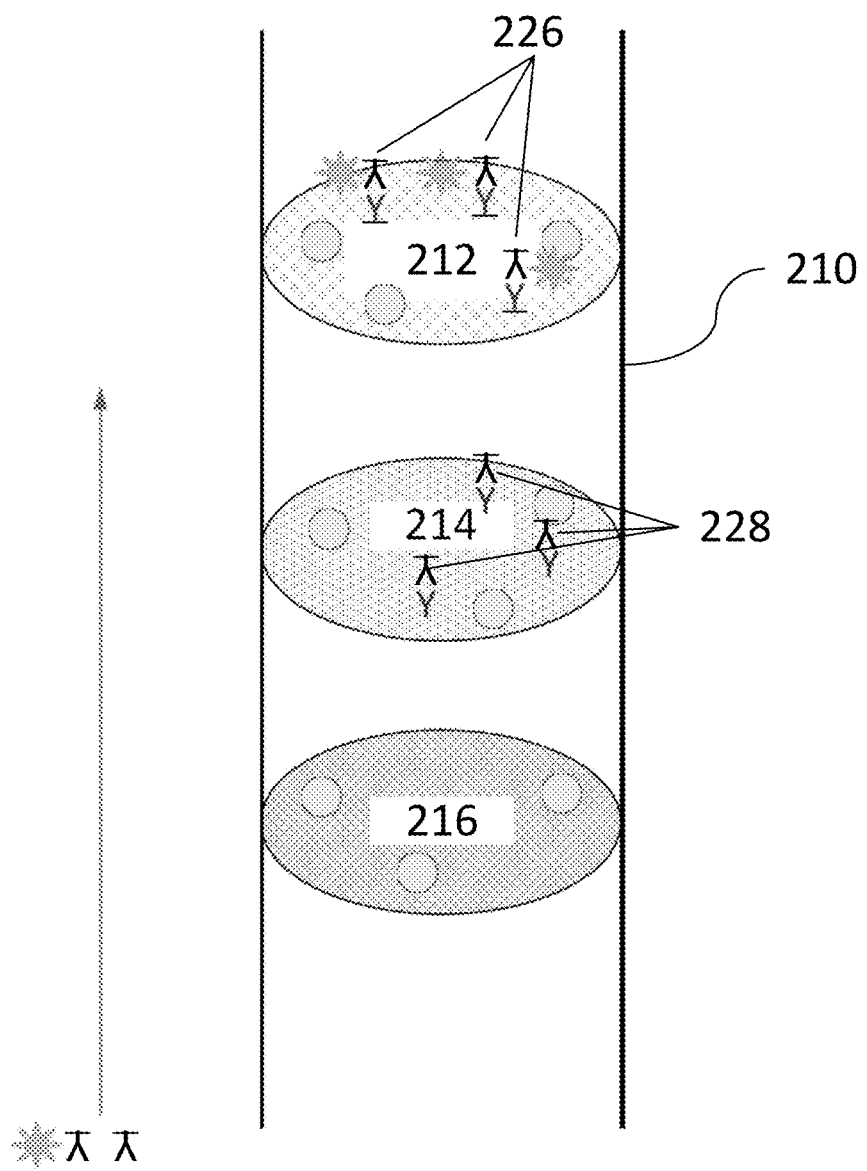
Figure 2E:
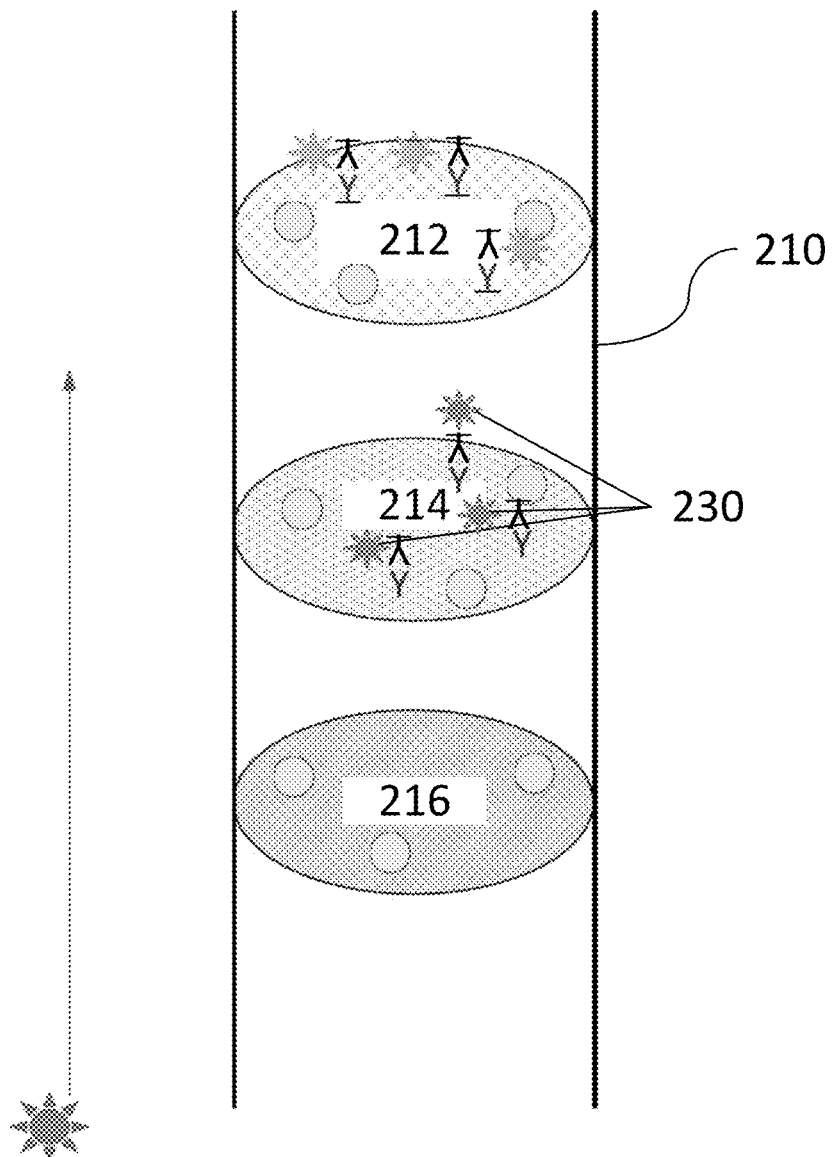

FIG. 2D illustrates the introduction of a first secondary antibody 226 and a second secondary antibody 228 to the capillary 210. The first secondary antibody 226 is configured to selectively bind to the first primary antibody 222, and the second secondary antibody 228 is configured to selectively bind to the second primary antibody 224. The first secondary antibody 226 and/or the second secondary antibody 228 can have, or be modified to have, optically detectable characteristics. For example, secondary antibodies can be labeled with optically detectable agents either before or after being introduced into the capillary. In some instances, it may be desirable for different secondary antibodies, which are configured to be associated with particular primary antibodies and therefore particular analyte species, to have different optical characteristics. For example, FIG. 2D illustrates a first secondary antibody 226 that is labeled with an optically detectable marker (e.g., a fluorescent dye) prior to introduction to the capillary 210. Optionally, unbound secondary antibodies and/or optically detectable agents can be washed from the capillary 210. The second secondary antibody 228, can be labeled, for example with HRP, prior to being introduced into the capillary 210. FIG. 2E illustrates the introduction of chemiluminescent substrate configured to interact with the HRP-labeled second secondary antibody 228 to produce an optically detectable signal. Optical characteristics associated with secondary antibodies, for example, chemiluminescence and fluorescence signals, can be collected by a CCD camera or another appropriate detector instantaneously and/or over time. Such optical signals can be used to identify some or all analyte species present in the sample. For example, as shown in FIG. 2E analyte species 212 and 214 would be detectable during an immunoassay. In instances in which one analyte species is associated with HRP and another analyte species is associated with a fluorescent dye (e.g., as shown in FIGS. 2C-2E), the chemiluminescent signal and the fluorescent signal can be detected simultaneously or sequentially. For example, the fluorescent labeled first secondary antibody 226 can be excited before, during, or after the introduction of the chemiluminescent substrate.

Figure 2F:
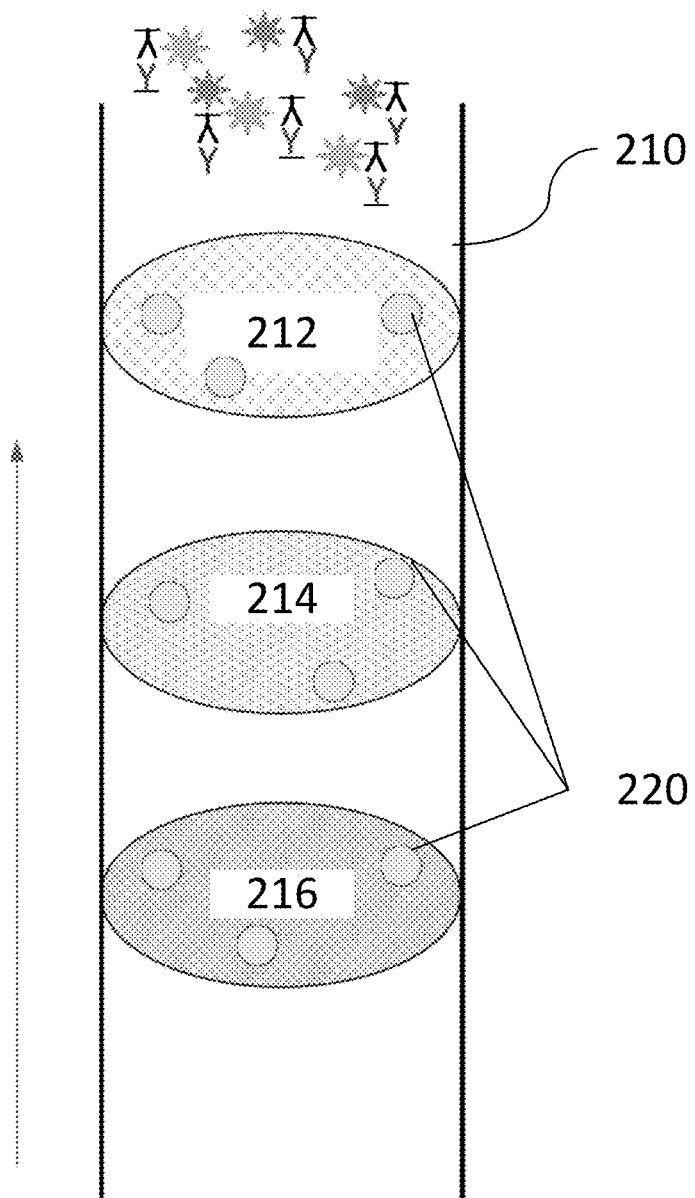
Figure 2G:
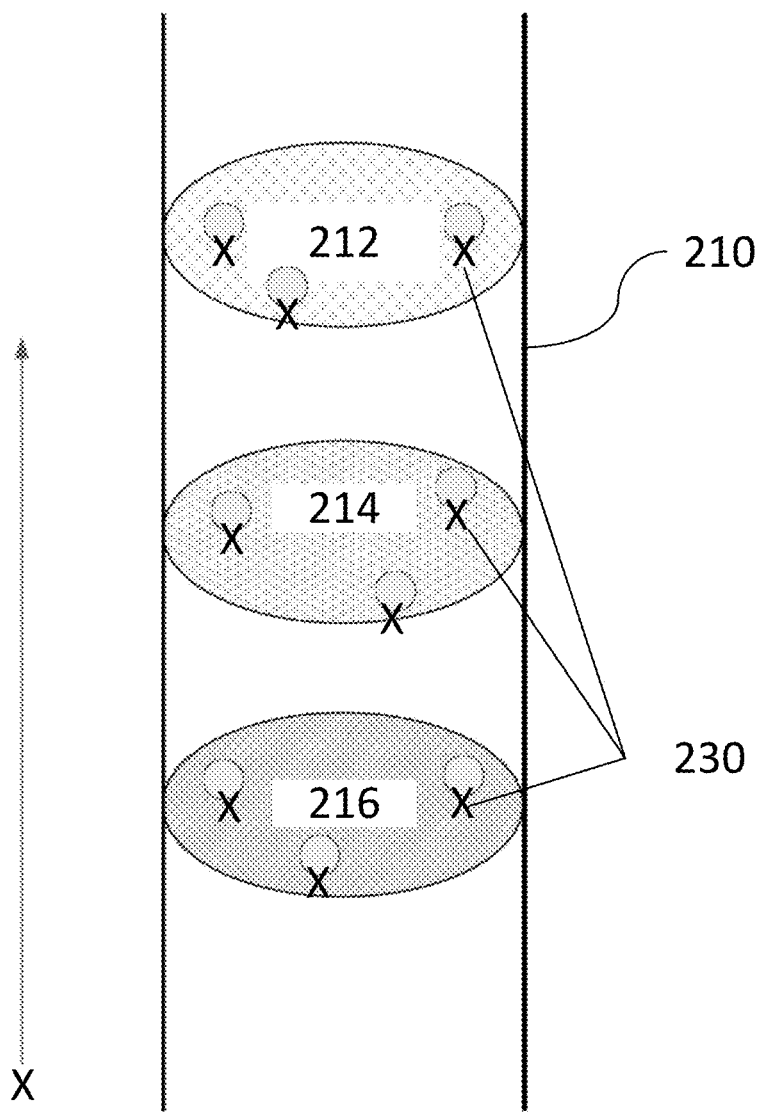
Figure 2H:
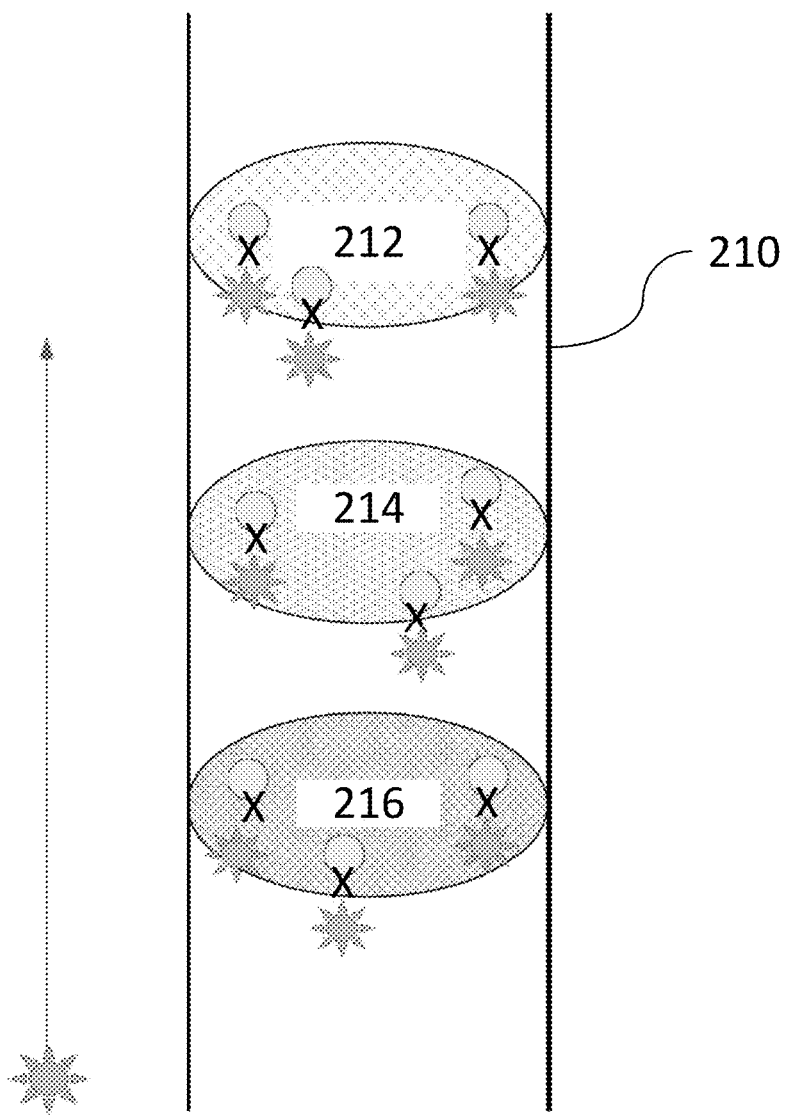

As shown in FIG. 2F, once the optical characteristics of the secondary antibodies are detected, a stripping reagent configured to remove primary and/or secondary antibodies from the analytes can be introduced into the capillary 210. The stripping reagent is configured to leave the biotin 220 bound to the analytes. FIG. 2G illustrates the introduction of streptavidin 232, avidin, and/or other suitable reagent configured to specifically bind to biotin into the capillary. The streptavidin can be HRP-conjugated (before or after introduction into the capillary 210) and/or otherwise labeled or optically detectable. Total protein detection can occur (e.g., a quantity of each protein labeled with biotin can be determined), for example, by loading a chemiluminescent substrate and detecting chemiluminescence signal, as shown in FIG. 2H. In some instances, a quantity of protein in each band can be determined separately.

Determining a total quantity of protein can allow for normalization of the immunoassay signal to the total protein content. Similarly stated, optical signals associated with immunoassay(s) (e.g., signals associated with secondary antibodies bound to analyte species through primary antibodies) can be corrected or normalized based on optical signals indicative of a quantity of the protein (e.g., the optical signal associated with streptavidin bound to proteins through biotin). In some instances, a reference capillary (not shown) can be loaded with a reference sample that is suitable for correcting immunoassay signals. For example, a cartridge containing multiple capillaries (e.g., capillary 210 and the reference capillary) can be loaded with sample(s) sequentially or in parallel. Proteins in each capillary can be biotinylated (sequentially or in parallel). HRP-conjugated streptavidin or another suitable reagent can be introduced into the capillaries (sequentially or in parallel). A chemiluminescent substrate can also be introduced into the capillaries (sequentially or in parallel) such that a total protein quantity in each capillary can be determined. In some embodiments, analytes detected via immunoassay in capillary 210 can be normalized based on the total protein content in the reference capillary. For example, a ratio of total protein in the reference capillary to total protein in capillary 210 can be determined. That ratio can be used to correct a signal associated with an immunoassay of an individual protein species. Such a technique can be used to correct immunoassay signals to account for loading heterogeneity. Similarly stated, a strong immunoassay signal could be the result of a "true" signal associated with a high concentration of a protein of interest relative to other proteins in the sample, or it could be associated with a large total quantity of protein, for example if the contents of more cells than expected were loaded into the capillary.

Typically, an analyst will prepare a sample and/or suitable reagents and load a reagent/sample plate prior to initiating an immunoassay and/or total protein measurement. In some embodiments, after initiating an immunoassay and/or total protein measurement, some or all subsequent events (e.g., sample load, separation, immunoassay or total protein, detection) can be performed automatically and/or without further interaction by the analyst. As would be readily apparent to one skilled in the art, additional stripping and reprobing steps are possible, additional intermediate wash steps may be performed to flush unbound reagents from the capillary, different combinations of detection modes may be used, and/or alternate detection modalities (color detection, fluorescence detection, etc.) can be used instead of the exact combination described in the embodiment above. While FIGS. 2A-2H describes detect two distinct protein species via chemiluminescence and fluorescence, followed by a total protein measurement, one skilled in the art would readily understand that an alternate embodiment could employ two different antibodies for the same target or two different epitopes of the same protein. In addition, fluorescence detection, absorbance or any suitable well-known detection method may be employed, including combinations of multiple detection modes.

FIGS. 2C and 2D illustrate introducing multiple primary antibodies 222, 224 substantially simultaneously (e.g., as a mixture) and illustrating multiple secondary antibodies 226, 228 substantially simultaneously. In contrast, FIGS. 1B-1G illustrate introducing different primary and secondary antibodies sequentially, with a stripping event occurring between the introduction of the first secondary antibody 122 and the introduction of the second primary antibody 130. It should be understood, however, that the method shown and described with respect to FIGS. 1A-H can include the introduction of a mixture of primary antibodies and/or secondary antibodies. Similarly, the method shown and described with respect to FIGS. 2A-2H can include sequential immunoassays, for example, with additional striping events between immunoassays.

According to some embodiments, methods described herein can be performed on an instrument suitable to conduct measurements of protein content and/or perform immunoassay in the same capillary and/or in an automated fashion, such as the Simple Western® platform by ProteinSimple®. Unlike other known instruments, and techniques, embodiments described herein are generally simpler than traditional methods used for total protein measurement for traditional western blots. Immunoassay and total protein measurements can be performed using chemiluminescent or fluorescent methods or other methods known in the art. In addition, the stripping reagent used to remove the antibodies from the immunoassay improve the accuracy of detection of the total protein content immobilized to the capillary.

As discussed above with reference to FIGS. 1A-1H, a skilled artisan would understand that the embodiment shown and described with reference to FIGS. 2A-2H are by way of example and not limitation. Specifically, a skilled artisan would understand that analyte species can be detected through any combination of chemiluminescent, fluorescent, and/or absorbance techniques. A skilled artisan would understand that additional or fewer than primary and secondary antibodies can be used. A skilled artisan would understand that antibodies can be pre-labeled with optically detectable agents, that optically detectable agents can be introduced into a capillary to selectively bind to antibodies and/or analyte species, and/or that analyte species and/or antibodies can be innately detectable (e.g., unlabeled antibodies can be detected, for example, based on their absorbance characteristics).

Order of Operations

As described previously, a specific order of reagent addition is preferred for improved performance when measuring Total Protein and immunoassay signal in a capillary. Experimental evidence demonstrates that addition of a biotinylation reagent after the immunoassay is complete resulted in signal that was 70% lower than a signal obtained when adding the biotinylation reagent prior to the immunoassay. It is important to maintain higher signal and thus sensitivity in this assay to obtained preferred detection levels for the assay. One could attempt to perform the complete Total Protein detection (e.g., biotinylation and detection using HRP conjugated streptavidin with luminol/peroxide) prior to the immunoassay, however, this is a less desirable assay configuration, presumably due to difficulty in removing the HRP conjugated streptavidin which has extremely high affinity for binding to biotin. Incomplete removal of the HRP conjugated streptavidin could negatively affect the immunoassay performance, for example, through residual HRP conjugated streptavidin bound to the biotinylated proteins preventing antibody binding to the target protein.

Stripping Reagent Formulation

There are a wide variety of formulations used for removal of antibodies from western blot membranes that are known in the art. These formulations typically comprise a buffering component, detergent, denaturant, acidic or basic pH, and/or reductant. Most stripping buffers known in the art use R-mercaptoethanol as a reductant, however, R-mercaptoethanol is toxic, not stable in solution, has an obnoxious smell, and its use is now restricted or banned in some countries. Accordingly, a need exists for a stripping reagent for removal of antibodies bound to analytes from a capillary.

An stripping reagent formulations using Tris(2-carboxyethyl)phosphine hydrochloride (TCEP) as a phosphine reductant in the place of R-mercaptoethanol have been developed and are shown in Table 1. While most of the Table 1 formulations tested worked to some extent in removing antibodies, it is desirable to consistently remove at least 95% of the residual signal of an immunoassay, for example, as performed using the Simple Western® instrument. Preferably the stripping reagent should also be stable in solution, i.e., no precipitation or decomposition should occur during storage over a period of time (e.g., 1 day, 1 week, 1 month, 6 months, 1 year, or any other suitable time frame). As can be seen in Table 1, merely substituting R-mercaptoethanol with TCEP failed to consistently achieve >95% stripping efficiency without precipitation. Achieving a high stripping efficiency across many antibodies is important because retained antibodies will create noise and degrade the limit of detection for subsequent immunoassay steps.

Figure 3:
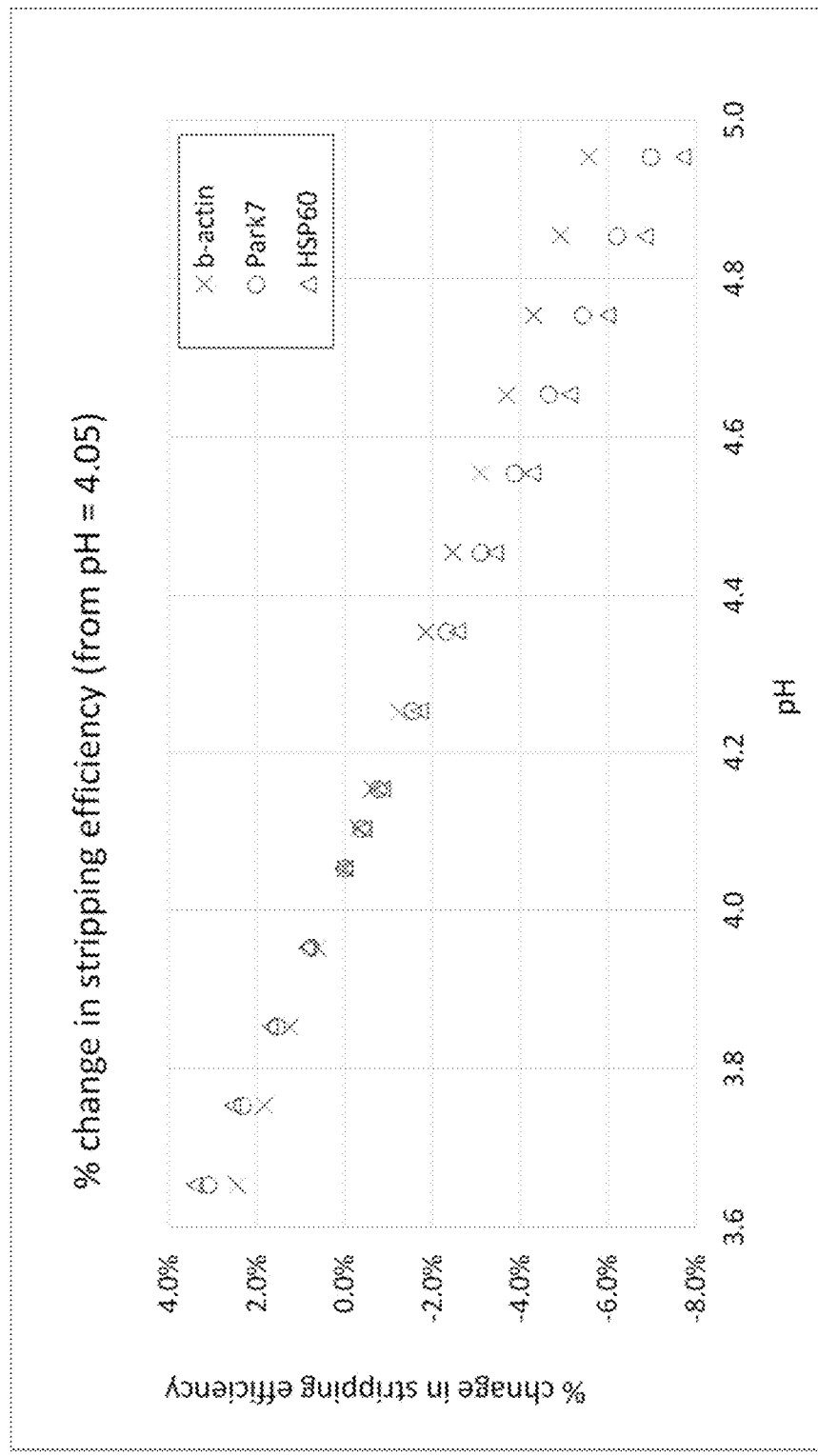
FIG. 3 illustrates stripping efficiency vs. pH for three different targets.

Further optimization was performed through broader titrations and new combinations of the components of Table 1 with additional components (such as different detergents and reductants). It has been determined that key influences on stripping efficiency include Trizma® (Tris base; CAS: 77-86-1) concentration, TCEP concentration and pH, while the stripping efficiency was relatively insensitive to SDS concentration. Formulations were analyzed for antibody removal efficiency on Simple Western® in combination with a variety of immunoassays (different antibodies, different target proteins), as shown in Table 2. Formulations were further tested for precipitation, decomposition, and ≥95% antibody removal efficiency for multiple antibodies. Several candidates in Table 2 meet these criteria. Formulations with neutral or basic pH performed significantly worse than formulations with acidic pH. This observation was surprising as TCEP is a reductant in the preferred formulations, and TCEP, according to conventional wisdom, is thought to be effective across a broad pH range of 1.5 to 8.5) with best reducing performance near neutral pH (i.e. near a pH of 7) (see Han, J. C. and Han, Y. H., *A Procedure for Quantitative Determination of tris(2-carboxyethyl)phosphine, an Odorless Reducing Agent More Stable and Effective Than Dithiothreitol*, Anal Biochem. 1994 July; 220(1):5-10, which is hereby incorporated by reference in its entirety). In addition, the preferred formulations were determined to operate with highest antibody removal efficiency in a narrow pH range, as shown in FIG. 3, which illustrates that preferred formulations capable of producing a stripping efficiency of >97% have pH of 4.05+/−0.3. FIG. 3 illustrates stripping efficiency against three different targets, park7, beta-actin, and HSP60.

TABLE 1

| Buffer | Denatured agents | Detergents | Reducing agents | Strong base | Stripping efficiency | Precipitates over time |
|---|---|---|---|---|---|---|
| 1XPBS | 0.1% SDS | 1% Tween | 50 mM TCEP | 0.1M NaOH | <50% | Yes |
| 1.5% glycine HCl, pH 2.2 (adjusted) | 0.1% SDS | 1% Tween | | | <70% | No |
| 1.5% glycine HCl | 0.1% SDS | 1% Tween | 50 mM TCEP | 0.2M NaOH | >70% | No |
| 60 mM TrisCl pH 7.2 | 2% SDS | | 10 mM THPP | | >70% | No |
| 60 mM TrisCl pH 7.2 | 2% SDS | | 10 mM TCEP | | >80% | No |
| 1.5% glycine HCl, pH 2.2 (adjusted) | 2% SDS | 1% Tween | | 0.2M NaOH | >90% | Yes |
| 0.1M TrisCl ph 7.2 | 0.1% SDS | 1% Tween | 50 mM TCEP | 0.1M NaOH | >90% | Yes |
| 0.1M TrisCl ph 7.2 | 0.1% SDS | 1% Tween/ 1% TritonX | 50 mM TCEP | 0.1M NaOH | >90% | Yes |
| 0.1M TrisCl ph 7.2 | 0.2% SDS | 1% Tween | 50 mM TCEP | 0.1M NaOH | >90% | Yes |
| 60 mM TrisCl pH 7 | 2% SDS | | 50 mM TCEP | | >90% | No |
| 60 mM TrisCl pH 7 | 2% SDS/10% TMP | | 50 mM TCEP | | >90% | No |

(THPP is Tris(hydroxypropyl)phosphine; TCEP is Tris(2-carboxyethyl)phosphine hydrochloride; Tween ® is Polysorbate 20 (CAS: 9005-64-5); Triton ® X-100 is t-Octylphenoxypolyethoxyethanol (CAS: 9002-93-1))

TABLE 2

| Buffer species | Conc mM | TCEP mM | TCEP stock | THPP mM | SDS | final pH | other detergents | Precipitation | % Stripping Efficiency | Stability at 60 C.: efficiency decrease |
|---|---|---|---|---|---|---|---|---|---|---|
| Trizma pH9 | 100 | | | 100 | 2% | 9 | | no | 14.1% | n/a |
| Trizma pH9 | 50 | | | 100 | 2% | 9 | | no | 19.5% | n/a |
| Trizma pH9 | 100 | | | 50 | 2% | 9 | | no | 31.3% | n/a |
| Trizma pH9 | 50 | | | 50 | 2% | 9 | | no | 32.5% | n/a |
| Trizma pH9 | 200 | | | 50 | 2% | 9 | | no | 34.3% | n/a |
| Trizma pH9 | 200 | | | 100 | 2% | 9 | | no | 34.5% | n/a |
| Glycine HCl pH3 | 50 | | | 100 | 2% | 7 | | no | 39.5% | n/a |
| Trizma pH9 | 500 | 100 | powder | | 2% | 8 | | no | 42.2% | n/a |
| MOPS | 200 | 100 | solution pH7 | | 2% | 6 | | no | 64.6% | n/a |
| MES | 200 | 100 | solution pH7 | | 2% | 5.5 | | no | 81.0% | n/a |
| Glycine HCl pH3 | 200 | | | 50 | 2% | 2.5 | | no | 91.6% | n/a |
| Glycine HCl pH3 | 50 | 100 | solution pH7 | | 2% | 4.5 | | 4C 1 day - yes, RT - no | 91.8% | n/a |
| Glycine HCl pH3 | 100 | | | 50 | 2% | 3 | | no | 93.4% | n/a |
| Glycine HCl pH3 | 200 | 100 | solution pH7 | | 2% | | CHAPS 2% | no | 94.4% | n/a |
| Glycine HCl pH3 | 200 | 100 | powder | | 2% | 2 | | no | 95.5% | n/a |
| Trizma pH9 | 200 | 100 | powder | | 2% | | CHAPS 2% | no | 95.9% | n/a |
| Glycine HCl pH3 | 200 | 100 | solution pH7 | | 2% | | TritonX-100 2% | no | 97.1% | n/a |
| TrisCl pH7.5 | 60 | 100 | powder | | 2% | 2.5 | | no | 97.4% | n/a |
| Glycine HCl pH3 | 200 | 100 | solution pH7 | | 2% | | Tween20 2% | no | 97.8% | n/a |
| Glycine HCl pH3 | 50 | n/a | | 50 | 1% | | n/a | no | 97.8% | n/a |
| Glycine HCl pH3 | 200 | | | 100 | 2% | 3 | | no | 97.8% | n/a |
| MES | 60 | 100 | powder | | 2% | | | no | 97.9% | n/a |
| MOPS | 60 | 100 | powder | | 2% | | | no | 97.9% | n/a |
| TrisCl pH7.5 | 60 | 50 | powder | | 2% | | | no - 4C/37C | 98.2% | week 2 - 70% |
| TrisCl pH7.5 | 60 | 75 | powder | | 2% | | | yes - 60C, 2 weeks | 98.2% | week 1 - 80% |
| Glycine HCl pH3 | 200 | 100 | solution pH7 | | 2% | | BRIJ 35 2% | no | 98.2% | n/a |
| Tricine | 60 | 100 | powder | | 2% | | | no | 98.3% | n/a |
| TrisCl pH7.5 | 60 | 100 | powder | | 2% | | | yes - 60C, 2 weeks | 98.4% | week 1 - 80% |
| Glycine HCl pH3 | 100 | 100 | solution pH7 | | 2% | 4 | | 4C 1 day - yes, RT - no | 98.4% | n/a |
| HEPES | 50 | 100 | powder | | 2% | 3 | | no | 98.4% | n/a |
| HEPES | 60 | 100 | powder | | 2% | 3 | | 4C 2 days - yes | 98.5% | n/a |
| Glycine HCl pH3 | 100 | | | 100 | 2% | 4.5 | | no | 98.5% | n/a |
| Trizma pH9 | 200 | 100 | powder | | 2% | | Tween20 2% | no | 98.5% | n/a |
| TrisCl pH7.5 | 60 | 150 | powder | | 2% | | | yes - 60C, 2 weeks | 98.5% | week 1 - 65% |
| Trizma pH9 | 60 | 100 | powder | | 2% | 2.5 | | no | 98.6% | n/a |
| HEPES | 75 | 100 | powder | | 2% | 3 | | 4C 1 day - yes | 98.6% | n/a |
| Glycine HCl pH3 | 50 | n/a | | 50 | 2% | | n/a | no | 98.6% | n/a |
| Trizma pH9 | 200 | 100 | powder | | 2% | | BRIJ 35 2% | no | 98.7% | n/a |
| Glycine HCl pH3 | 50 | n/a | | 50 | | | 1% LDS | no | 98.7% | n/a |
| HEPES | 200 | 100 | powder | | 2% | 3.5 | | 4C 4 days - yes | 98.7% | n/a |
| HEPES | 200 | 100 | powder | | 2% | 3.5 | | 4C 1 day - yes | 98.7% | n/a |
| HEPES | 150 | 100 | powder | | 2% | 3 | | 4C 1 day - yes | 98.8% | n/a |
| Trizma pH9 | 200 | 100 | powder | | 2% | | TritonX-100 2% | no | 98.8% | n/a |
| Glycine HCl pH3 | 200 | 100 | solution pH7 | | 2% | | Tween20 0.5% | no | 98.8% | n/a |
| Glycine HCl pH3 | 50 | n/a | | 50 | | | 2% LDS | no | 98.9% | n/a |
| HEPES | 100 | 100 | powder | | 2% | 3 | | 4C 1 day - yes | 98.9% | n/a |
| Trizma pH9 | 75 | 100 | powder | | 2% | | | no | 98.9% | n/a |
| Glycine HCl pH3 | 200 | 100 | solution pH7 | | 2% | | TritonX-100 0.5% | no | 99.0% | n/a |
| Trizma pH9 | 50 | 100 | powder | | 2% | 3 | | no | 99.0% | n/a |
| Glycine HCl pH3 | 50 | n/a | | 50 | 5% | | n/a | no | 99.0% | n/a |
| Glycine HCl pH3 | 200 | 100 | solution pH7 | | 2% | | CHAPS 0.5% | no | 99.0% | n/a |
| Trizma pH9 | 200 | 100 | powder | | 2% | | CHAPS 0.5% | no | 99.0% | n/a |
| Glycine HCl pH3 | 200 | 100 | solution pH7 | | 2% | 3.5 | | 4C 1 day - yes; RT - no | 99.1% | week 2: no decrease |
| Glycine HCl pH3 | 200 | 100 | solution pH7 | | 2% | | BRIJ 35 0.5% | no | 99.1% | n/a |
| Trizma pH9 | 200 | 100 | powder | | 2% | | TritonX-100 0.5% | no | 99.1% | n/a |
| Glycine HCl pH3 | 200 | 100 | solution pH7 | | | | 1% LDS | no | 99.1% | n/a |
| Bicine | 50 | 100 | powder | | 2% | 3 | | no | 99.1% | n/a |
| Glycine HCl pH3 | 200 | 100 | solution pH7 | | 1% | | | no | 99.1% | n/a |
| Glycine HCl pH3 | 200 | 100 | solution pH7 | | | | 2% LDS | no | 99.1% | n/a |
| Glycine HCl pH3 | 200 | 100 | solution pH7 | | 2% | | | no | 99.2% | n/a |
| Glycine HCl pH3 | 50 | n/a | | 50 | | | 5% LDS | no | 99.2% | n/a |
| Trizma pH9 | 200 | 100 | powder | | 1% | | | no | 99.2% | n/a |
| Trizma pH9 | 200 | 100 | powder | | | | 5% LDS | no | 99.2% | n/a |
| Trizma pH9 | 200 | 100 | powder | | 2% | | Tween20 0.5% | no | 99.2% | n/a |
| Trizma pH9 | 200 | 100 | powder | | | | 2% LDS | no | 99.2% | n/a |
| Trizma pH9 | 100 | 100 | powder | | 2% | | | no | 99.2% | n/a |
| Trizma pH9 | 200 | 100 | powder | | 2% | | | no | 99.2% | n/a |

TABLE 2-continued

| Buffer species | Conc mM | TCEP mM | TCEP stock | THPP mM | SDS | other final pH detergents | Precipitation | % Stripping Efficiency | Stability at 60 C.: efficiency decrease |
|---|---|---|---|---|---|---|---|---|---|
| Bicine | 150 | 100 | powder | | 2% | 3 | no | 99.2% | n/a |
| Trizma pH9 | 200 | 100 | powder | | 5% | | yes - 4C 3days, goes back to soln in RT | 99.2% | n/a |
| Trizma pH9 | 200 | 100 | powder | | | 1% LDS | no | 99.3% | n/a |
| Bicine | 100 | 100 | powder | | 2% | 3 | no | 99.3% | n/a |
| Trizma pH9 | 200 | 100 | powder | | 2% | BRIJ 35 0.5% | no | 99.3% | n/a |
| Trizma pH9 | 150 | 100 | powder | | 2% | | no | 99.3% | n/a |
| Glycine HCl pH3 | 200 | 100 | solution pH7 | | 5% | | no | 99.3% | n/a |
| Trizma pH9 | 200 | 100 | powder | | 2% | 4 | no | 99.3% | n/a |
| Glycine HCl pH3 | 200 | 100 | solution pH7 | | | 5% LDS | no | 99.4% | n/a |
| Glycine HCl pH3 | 50 | | | 50 | 2% | 4 | no | 99.5% | week 2: no decrease |

(BRIJ ™ 35 (also known as BRIJ ™ L23) is a 30% solution of Polyoxyethylene (23) lauryl ether (CAS: 9002-92-0))

Figure 4:
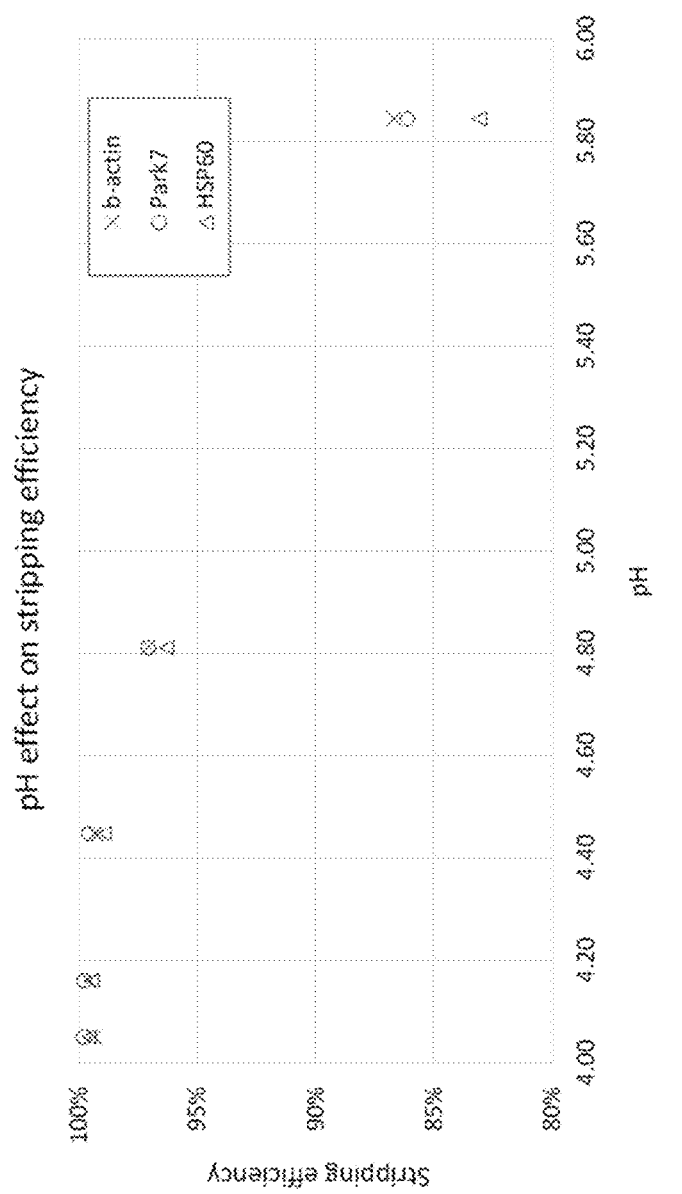
FIG. 4 illustrates stripping efficiency vs. a wider pH range demonstrating a significant reduction in stripping efficiency at pH>4.5.

FIG. 4 illustrates the performance of the formulations shown in Table 3 and shows an even greater decrease in stripping efficiency when the pH is greater than 4.5. A less severe, but noticeable decrease in stripping efficiency when the pH was less than 3 (data not shown in FIG. 4, but apparent from individual rows of Table 2). It was surprising to discover that a narrow and specific pH range was required for optimal antibody removal 95%) in the Simple Western® capillary. This may be due to the unique properties and/or internal environment of the Simple Western capillary versus a western blot membrane. Also, it was determined that multiple incubations of the stripping reagent in the capillary improved antibody removal efficiency.

TABLE 3

| | Trizma, m | SDS % | TCEP, mM | pH | b-actin | Park7 | HSP60 |
|---|---|---|---|---|---|---|---|
| A | 240 | 2.0% | 80 | 5.84 | 86.73% | 86.13% | 83.10% |
| B | 220 | 2.0% | 80 | 4.81 | 97.07% | 97.07% | 96.32% |
| C | 200 | 2.0% | 80 | 4.45 | 99.32% | 99.59% | 98.94% |
| D | 220 | 2.0% | 100 | 4.16 | 99.62% | 99.78% | 99.46% |
| Center Po | 200 | 2% | 100 | 4.05 | 99.36% | 99.82% | 99.59% |

While various embodiments have been described above, it should be understood that they have been presented by way of example only, and not limitation. For example, while embodiments described herein generally describe capillary-based techniques, it should be understood that any suitable microfluidic device or other electrophoretic techniques can be used. As another example, embodiments described herein related to Total Protein labeling generally describe biotinylation. It should be understood, however, that other suitable techniques for non-specific protein labeling and detection are also possible, such as, his-tag/anti-his, glutathione/glutathione s-transferase, maltose/maltose-binding protein, chitin/chitin-binding protein, etc. A person skilled in the art would understand that any suitable molecule having an NHS-ester or other moiety to chemically react with proteins (e.g., amino acids such as lysine, protein backbones such as nitrogen, post-translation modifications like glycan, etc.) could be suitable for Total Protein labeling. In addition, while techniques to identify a total quantity of proteins and normalize based on protein quantity have been described, it should be understood that analogous techniques exist for many other analytes. For example, it is possible to perform a measurement of the total amount of nucleic acid, lipid, and/or glycoprotein, which can then be used to normalize measurements between capillaries. For example, a molecule having an aminooxy reactive group can chemically react with sugars such as polysaccharides or glycan groups. Likewise a molecule having a psoralen group can bind with DNA or RNA via UV-light-activated intercalation of the psoralen group with thymine- and other pyrimidine-containing bases. Nucleic acid binding chemistries include the carbodiimide crosslinker EDC/imidazole as well as other chemical and enzymatic attachment methods known in the art. Likewise, methods to biotinylate lipids are known in the art, see for example Henry, Stephen, et al. 'Rapid one-step biotinylation of biological and non-biological surfaces.' Scientific reports 8.1 (2018): 1-6," the entire disclosure of which is hereby incorporated by reference.

Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed is:

1. A method, comprising:
electrophoretically separating a sample containing a plurality of analytes in a microfluidic device;
immobilizing the plurality of analytes in the microfluidic device;
introducing a first primary antibody into the microfluidic device, the first primary antibody capable of binding to a first analyte from the plurality of analytes;
introducing a secondary antibody into the microfluidic device, the secondary antibody capable of binding to the first primary antibody;
stripping the first primary antibody from the first analyte using a reagent having a pH between 3 and 4.5 and including Tris(2-carboxyethyl)phosphine hydrochloride) (TCEP); and introducing into the microfluidic device and after stripping the first primary antibody from the first analyte at least one of (i) a second primary antibody capable of binding to a second analyte from the plurality of analytes or (ii) streptavidin capable of non-specifically binding to the plurality of analytes.

2. The method of claim 1, wherein the reagent includes a buffer selected from the group consisting of:
Tris base;
Glycine HCl;
4-(2-hydroxyethyl)-1-piperazineethanesulfonic acid (HEPES); and
Bicine.

3. The method of claim 1, wherein the reagent has a stripping efficiency of greater than 95% and includes a buffer formulation comprising a buffer selected from the group consisting of:
100 mM Glycine hydrochloride (HCl), 100 mM Tris(2-carboxyethyl)phosphine hydrochloride (TCEP); 2% sodium dodecyl sulfate (SDS);
200 mM Tris base, 100 mM TCEP, 2% SDS, 2% 3-[(3-cholamidopropyl)dimethylammonio]-1-propane-sulfonate (CHAPS);
200 mM Glycine HCl, 100 mM TCEP, 2% SDS, 2% t-Octylphenoxypolyethoxyethanol;
60 mM Tris hydrocholoride (TrisCl), 100 mM TCEP, 2% SDS;
200 mM Glycine HCl, 100 mM TCEP, 2% SDS, 2% Polysorbate 20;
60 mM 2-(N-morpholino)ethanesulfonic acid (MES), 100 mM TCEP, 2% SDS;
60 mM 3-(N-morpholino)propanesulfonic acid (MOPS), 100 mM TCEP, 2% SDS;
60 mM TrisCl, 50 mM TCEP, 2% SDS;
60 mM TrisCl, 75 mM, TCEP, 2% SDS;
200 mM Glycine HCl, 100 mM TCEP, 2% SDS, 2% Polyoxyethylene (23) lauryl ether;
60 mM N-(2-Hydroxy-1,1-bis(hydroxymethyl)ethyl)glycine (Tricine), 100 mM TCEP, 2% SDS;
60 mM TrisCl, 100 mM TCEP, 2% SDS;
100 mM Glycine HCl, 100 mM TCEP, 2% SDS;
50 mM 4-(2-hydroxyethyl)-1-piperazineethanesulfonic acid) (HEPES), 100 mM TCEP, 2% SDS;
60 mM HEPES, 100 mM TCEP, 2% SDS, 2% Polysorbate 20;
60 mM TrisCl, 150 mM TCEP, 2% SDS;
60 mM Tris base, 100 mM TCEP, 2% SDS;
75 mM HEPES, 100 mM TCEP, 2% SDS;
200 mM Tris base, 100 mM TCEP, 2% SDS, 2% Polyoxyethylene (23) lauryl ether;
200 mM HEPES, 100 mM TCEP, 2% SDS;
150 mM HEPES, 100 mM TCEP, 2% SDS;
200 mM Tris base, 100 mM TCEP, 2%;
200 mM Glycine HCl, 100 mM TCEP, 2% SDS, 0.5% Polysorbate 20;
100 mM HEPES, 100 mM TCEP, 2% SDS;
75 mM Tris base, 100 mM TCEP, 2% SDS;
200 mM Glycine HCl, 100 mM TCEP, 2% SDS, 0.5% t-Octylphenoxypolyethoxyethanol;
50 mM Tris base, 100 mM TCEP, 2% SDS;
200 mM Glycine HCl, 100 mM TCEP, 2% SDS, 0.5% CHAPS;
200 mM Tris base, 100 mM TCEP, 2% SDS, 0.5% CHAPS;
200 mM Glycine HCl, 1200 mM TCEP, 2% SDS;
200 mM Glycine HCl, 1200 mM TCEP, 2% SDS, 0.5% Polyoxyethylene (23) lauryl ether;
200 mM Tris base, 100 mM TCEP, 2% SDS, 0.5% t-Octylphenoxypolyethoxyethanol;
200 mM Glycine HCl, 100 mM TCEP, 1% lithium dodecyl sulfate (LDS);
50 mM Bicine 1'00 mM TCEP; 2% SDS;
200 mM Glycine HCl, 100 mM TCEP, 1% SDS;
200 mM Glycine HCl, 100 mM TCEP, 2% LDS;
200 mM Glycine HCl, 100 mM TCEP, 2% SDS;
200 mM Tris base, 100 mM TCEP, 1% SDS;
200 mM Tris base, 100 mM TCEP, 5% LDS;
200 mM Tris base, 100 mM TCEP, 2% SDS, 0.5% Polysorbate 20;
200 mM Tris base, 100 mM TCEP, 2% LDS;
100 mM Tris base, 100 mM TCEL, 2% SDS;
150 mM Bicine, 100 mM TCEP, 2% SDS;
200 mM Tris base, 100 mM TCEP, 5% SDS;
200 mM Tris base, 100 mM TCEP, 1% LDS;
100 mM Bicine, 100 mM TCEP, 2% SDS, 0.5% Polyoxyethylene (23) lauryl ether;
150 mM Tris base, 100 mM TCEP, 2% SDS;
200 mM Glycine HCl, 100 mM TCEP, 5% SDS;
200 mM Tris base, 100 mM TCEP, 2% SDS; and
200 mM Glycine HCl, 100 mM TCEP, 5% LDS.

4. The method of claim 1, wherein streptavidin capable of non-specifically binding to the plurality of analytes is introduced into the microfluidic device after stripping the first primary antibody from the first analyte, the method further comprising:
biotinylating the plurality of analytes after immobilizing the plurality of analytes and before introducing the first primary antibody.

5. The method of claim 1, wherein streptavidin capable of non-specifically binding to the plurality of analytes is introduced into the microfluidic device after stripping the first primary antibody from the first analyte, the method further comprising:
biotinylating the plurality of analytes after immobilizing the plurality of analytes and before introducing the first primary antibody;
detecting the first analyte based on an optical signal associated with the secondary antibody;
detecting an optical signal associated with a luminescent agent conjugated to the streptavidin;
determining a quantity of the plurality of analytes based on the optical signal associated with the luminescent agent; and
normalizing the optical signal associated with the secondary antibody based on the quantity of the plurality of analytes.

6. The method of claim 1, wherein the microfluidic device is a capillary.

* * * * *

UNITED STATES PATENT AND TRADEMARK OFFICE
CERTIFICATE OF CORRECTION

PATENT NO. : 11,237,164 B2
APPLICATION NO. : 16/932445
DATED : February 1, 2022
INVENTOR(S) : Irina Georgievna Kazakova et al.

It is certified that error appears in the above-identified patent and that said Letters Patent is hereby corrected as shown below:

In the Claims

Column 17, Claim 3, Line 18 reads:
100 mM Glycine hydrochloride (HC1), 100 mM Tris(2-
Whereas it should read:
200 mM Glycine hydrochloride (HC1), 100 mM Tris(2-

Column 18, Claim 3, Line 5-6 reads:
200 mM Glycine HC1, 1200 mM TCEP, 2% SDS;
200 mM Glycine HC1, 1200 mM TCEP, 2% SDS, 0.5%
Whereas it should read:
200 mM Glycine HC1, 100 mM TCEP, 2% SDS, 0.5%

Column 18, Claim 3, Line 12 reads:
50 mM Bicine 1'00 mM TCEP; 2% SDS;
Whereas it should read:
50 mM Bicine, 100 mM TCEP; 2% SDS;

Column 18, Claim 3, Line 25-26 reads:
100 mM Bicine, 100 mM TCEP, 2% SDS, 0.5% Polyoxyethylene
(23) lauryl ether;
Whereas it should read:
100 mM Bicine, 100 mM TCEP, 2% SDS;

Signed and Sealed this
Sixteenth Day of December, 2025

John A. Squires
*Director of the United States Patent and Trademark Office*